(12) United States Patent
Schoenafinger et al.

(10) Patent No.: US 7,138,414 B2
(45) Date of Patent: Nov. 21, 2006

(54) HETEROCYCLICALLY SUBSTITUTED BENZOYLUREAS, PROCESS FOR THEIR PREPARATION AND THEIR USE AS PHARMACEUTICALS

(75) Inventors: Karl Schoenafinger, Alzenau (DE); Elisabeth Defossa, Idstein (DE); Dieter Kadereit, Kelkheim (DE); Erich Von Roedern, Hattersheim (DE); Thomas Klabunde, Frankfurt (DE); Hans-Joerg Burger, Morristown, NJ (US); Andreas Herling, Bad Camberg (DE); Karl-Ulrich Wendt, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/617,498

(22) Filed: Jul. 11, 2003

(65) Prior Publication Data

US 2004/0152743 A1 Aug. 5, 2004

Related U.S. Application Data

(60) Provisional application No. 60/430,782, filed on Dec. 4, 2002.

(30) Foreign Application Priority Data

| Jul. 12, 2002 | (DE) | ................... 102 31 627 |
| Feb. 17, 2003 | (DE) | ................... 103 06 503 |
| May 6, 2003 | (DE) | ................... 103 20 326 |

(51) Int. Cl.
| C07D 235/02 | (2006.01) |
| C07D 251/00 | (2006.01) |
| A61K 31/395 | (2006.01) |
| A61K 31/445 | (2006.01) |

(52) U.S. Cl. ................... 514/317; 514/210.1; 514/241; 514/242; 514/317; 514/364; 514/381; 514/383; 514/394; 514/406; 514/408; 514/461; 544/180; 546/192; 548/131; 548/253; 548/255; 548/262.2; 548/304.4; 548/375.1; 548/567; 548/950; 549/499

(58) Field of Classification Search ................ 514/317, 514/364, 394, 406, 210.1, 241, 242, 381, 514/383, 408, 461; 546/192; 548/131, 253, 548/304.4, 255, 567, 262.2, 375.1, 950; 544/180; 549/499

See application file for complete search history.

(56) References Cited

U.S. PATENT DOCUMENTS

| 6,221,633 B1 | 4/2001 | Ertl |
| 6,221,897 B1 | 4/2001 | Frick et al. |
| 6,245,744 B1 | 6/2001 | Frick et al. |
| 6,342,512 B1 | 1/2002 | Kirsch |

FOREIGN PATENT DOCUMENTS

| DE | 10116768 | 10/2002 |
| DE | 10142734 | 3/2003 |
| EP | 0193249 | 9/1986 |
| EP | 0 242 322 | 12/1992 |
| EP | 0 462 884 | 6/1993 |
| WO | WO 97/26265 | 7/1997 |
| WO | WO 97/41097 | 11/1997 |
| WO | WO 98/08871 | 3/1998 |
| WO | WO 99/03861 | 1/1999 |
| WO | WO 99/15525 | 4/1999 |
| WO | WO 00/40569 | 7/2000 |
| WO | WO 00/63208 | 10/2000 |
| WO | WO 00/64876 | 11/2000 |
| WO | WO 00/64888 | 11/2000 |
| WO | WO 00/66585 | 11/2000 |
| WO | WO 00/71549 | 11/2000 |
| WO | WO 00/78312 | 12/2000 |
| WO | WO 01/09111 | 2/2001 |
| WO | WO 01/83451 | 11/2001 |
| WO | WO 01/85695 | 11/2001 |
| WO | WO 01/91752 | 12/2001 |
| WO | WO 01/94300 | 12/2001 |
| WO | WO 01/94300 A1 * | 12/2001 |
| WO | WO 02/096864 | 12/2002 |

OTHER PUBLICATIONS

Asakawa A. et al., Cocaine-Amphetamine-Regulated Transcript Influences Energy Metabolism, Anxiety and Gastric Emptying In Mice, Hormones Metabolism Research, (2001), vol. 33, pp. 554-558.

(Continued)

*Primary Examiner*—Zinna N. Davis
(74) *Attorney, Agent, or Firm*—Barbara E. Kurys

(57) ABSTRACT

The invention relates to heterocyclically substituted benzoylureas and also to their physiologically tolerated salts and physiologically functional derivatives.

Compounds are described of the formula I

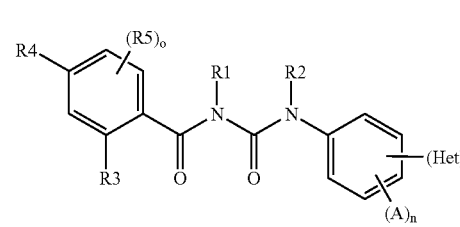

where the radicals are defined as specified, and also their pharmaceutically acceptable salts and processes for their preparation. The compounds are suitable, for example, for treating type 2 diabetes.

15 Claims, No Drawings

OTHER PUBLICATIONS

Drueckes P. et al., Photometric Microtiter Assay Of Inorganic Phosphate In The Presence Of Acid-Labile Organic Phosphate, Analytical Biochemistry, (1995), vol. 230, pp. 173-177.

Engers H.D. et al., Kinetic Mechanism Of Phosphorylase a. 1. Initial Velocity Studies, Journal Of Biochemistry, (1970), vol. 48, pp. 746-754.

Okada Hiroshi et al., Synthesis And Antitumor Activities Of Prodrugs Of Benzoylphenylureas, Chemical And Pharmaceuticals Bulletin, (1994), vol. 42, No. 1, pp. 57-61.

Salvador Javier et al., Perspectives In The Therapeutic Use Of Leptin, Expert Opinion On Pharmacotherapy, (2001), vol. 2, No. 10, pp. 1615-1622.

Tyle Praveen, Iontophoretic Devices For Drug Delivery, Pharmaceutical Research, (1986), vol. 3, No. 6, pp. 318-326.

Zunft H.J.F. et al., Carob Pulp Preparation For Treatment Of Hypercholesterolemia, Advances In Therapy, (2001), vol. 18, No. 5, pp. 231-236.

* cited by examiner

HETEROCYCLICALLY SUBSTITUTED BENZOYLUREAS, PROCESS FOR THEIR PREPARATION AND THEIR USE AS PHARMACEUTICALS

The invention relates to heterocyclically substituted benzoylureas and also to their physiologically tolerated salts and physiologically functional derivatives.

Heterocyclically substituted benzoylureas having pesticidal action have already been described in the prior art (EP 0 242 322).

It is an object of the invention to provide compounds which exert a therapeutically utilizable blood sugar-reducing action.

The invention therefore relates to compounds of the formula I,

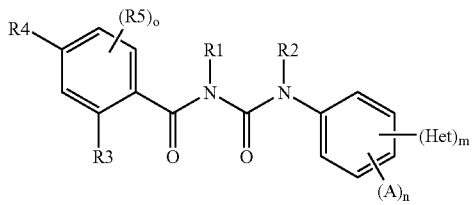

wherein
R1 and R2 are each independently H, O—$(C_1$–$C_6)$-alkyl, CO—$(C_1$–$C_6)$-alkyl, COO—$(C_1$–$C_6)$-alkyl, $(C_1$–$C_6)$-alkylene-COOH, $(C_1$–$C_6)$-alkylene-COO—$(C_1$–$C_6)$-alkyl or $(C_1$–$C_6)$-alkyl, wherein said $(C_1$–$C_6)$-alkyl may be substituted by OH, O—$(C_1$–$C_4)$-alkyl, $NH_2$, $NH(C_1$–$C_4)$-alkyl or $N[(C_1$–$C_6)$-alkyl$]_2$;

R3 and R4 are each independently F, Cl, Br, OH, $NO_2$, CN, $(C_1$–$C_6)$-alkyl, O—$(C_1$–$C_4)$-alkyl, O—$(C_2$–$C_6)$-alkenyl or $(C_2$–$C_6)$-alkynyl, wherein said $(C_1$–$C_6)$-alkyl, O—$(C_1$–$C_4)$-alkyl, O—$(C_2$–$C_6)$-alkenyl and $(C_2$–$C_6)$-alkynyl are optionally mono- or polysubstituted by F, Cl or Br;

R5 is H, F, Cl, Br, OH, $NO_2$, CN, $(C_1$–$C_6)$-alkyl, O—$(C_1$–$C_4)$-alkyl, CO—$(C_1$–$C_6)$-alkyl, $(C_0$–$C_6)$-alkylene-COOH, $(C_0$–$C_6)$-alkylene-COO—$(C_1$–$C_6)$-alkyl, $SO_2$—$(C_1$–$C_6)$-alkyl, O—$(C_2$–$C_6)$-alkenyl or $(C_2$–$C_6)$-alkynyl, wherein said $(C_1$–$C_6)$-alkyl, O—$(C_1$–$C_4)$-alkyl, CO—$(C_1$–$C_6)$-alkyl, $(C_0$–$C_6)$-alkylene-COOH, $(C_0$–$C_6)$-alkylene-COO—$(C_1$–$C_6)$-alkyl, $SO_2$—$(C_1$–$C_6)$-alkyl, O—$(C_2$–$C_6)$-alkenyl and $(C_2$–$C_6)$-alkynyl are optionally mono- or polysubstituted by F, Cl or Br;

A is H, F, Cl, Br, OH, $NO_2$, CN, $(C_1$–$C_6)$-alkyl, CO—$(C_1$–$C_6)$-alkyl, $(C_1$–$C_6)$-alkylene-COOH, $(C_1$–$C_6)$-alkylene-COO$(C_1$–$C_6)$-alkyl, $SO_2$—$(C_1$–$C_6)$-alkyl, $(C_2$–$C_6)$-alkenyl, $(C_2$–$C_6)$-alkynyl, O—$(C_1$–$C_6)$-alkyl, $S(O)_{1-2}$—$(C_1$–$C_6)$-alkyl-, NH—$(C_1$–$C_6)$-alkyl, N—$[(C_1$–$C_6)$-alkyl$]_2$, COOH, COO—$(C_1$–$C_6)$-alkyl, $CONH_2$, CONH—$(C_1$–$C_6)$-alkyl, CON—$[(C_1$–$C_6)$-alkyl$]_2$, $SO_2NH_2$, $SO_2NH$—$(C_1$–$C_6)$-alkyl, $SO_2N$—$[(C_1$–$C_6)$-alkyl$]_2$ or $NHCOR6$, wherein said $(C_1$–$C_6)$-alkyl, CO—$(C_1$–$C_6)$-alkyl, $(C_1$–$C_6)$-alkylene-COOH, $(C_1$–$C_6)$-alkylene-COO$(C_1$–$C_6)$-alkyl, $SO_2$—$(C_1$–$C_6)$-alkyl, $(C_2$–$C_6)$-alkenyl, $(C_2$–$C_6)$-alkynyl, O—$(C_1$–$C_6)$-alkyl, $S(O)_{1-2}$—$(C_1$–$C_6)$-alkyl-, NH—$(C_1$–$C_6)$-alkyl, N—$[(C_1$–$C_6)$-alkyl$]_2$, COO—$(C_1$–$C_6)$-alkyl, CONH—$(C_1$–$C_6)$-alkyl, CON—$[(C_1$–$C_6)$-alkyl$]_2$, $SO_2NH$—$(C_1$–$C_6)$-alkyl and $SO_2N$—$[(C_1$–$C_6)$-alkyl$]_2$ are optionally mono- or polysubstituted by F, Cl, Br, COOH, COO—$(C_1$–$C_6)$-alkyl, $CONH_2$, CONH—$(C_1$–$C_6)$-alkyl, CON$[(C_1$–$C_6)$-alkyl$]_2$ or OCO—$(C_1$–$C_6)$-alkyl;

R6 is H, $(C_1$–$C_6)$-alkyl, $(C_3$–$C_7)$-cycloalkyl, $(C_3$–$C_7)$-cycloalkyl-$(C_1$–$C_4)$-alkylene, $(C_2$–$C_6)$-alkenyl, $(C_2$–$C_6)$-alkynyl, $(C_1$–$C_6)$-alkylene-COO—$(C_1$–$C_6)$-alkyl, $(C_1$–$C_6)$-alkylene-CO—$(C_1$–$C_6)$-alkyl, $(C_0$–$C_6)$-alkylene-COOH, $(C_1$–$C_6)$-alkylene-$CONH_2$, $(C_6$–$C_{10})$-aryl, $(C_1$–$C_4)$-alkylene-$(C_6$–$C_{10})$-aryl, heteroaryl, $(C_1$–$C_4)$-alkylene-heteroaryl or CO-heteroaryl, wherein said $(C_1$–$C_6)$-alkyl, $(C_3$–$C_7)$-cycloalkyl, $(C_3$–$C_7)$-cycloalkyl-$(C_1$–$C_4)$-alkylene, $(C_2$–$C_6)$-alkenyl, $(C_2$–$C_6)$-alkynyl, $(C_1$–$C_6)$-alkylene-COO—$(C_1$–$C_6)$-alkyl, $(C_1$–$C_6)$-alkylene-CO—$(C_1$–$C_6)$-alkyl, $(C_0$–$C_6)$-alkylene-COOH and $(C_1$–$C_6)$-alkylene-$CONH_2$ are optionally mono- or polysubstituted by F, Cl, Br, $O(C_1$–$C_4$-alkyl), COO—$(C_1$–$C_4$-alkyl) or $N$—$[(C_1$–$C_4)$-alkyl$]_2$ and said $(C_6$–$C_{10})$-aryl, $(C_1$–$C_4)$-alkylene-$(C_6$–$C_{10})$-aryl, heteroaryl, $(C_1$–$C_4)$-alkylene-heteroaryl and CO-heteroaryl are optionally mono- or poly substituted by F, Cl, Br, $NO_2$, CN, O—$(C_1$–$C_4$-alkyl), S—COO$(C_1$–$C_4$-alkyl), COO—$(C_1$–$C_4$-alkyl), N—$[(C_1$–$C_4)$-alkyl$]_2$ or $(C_1$–$C_6)$-alkyl;

n is 0, 1, 2 or 3;
m is 1, 2, 3, 4 or 5;
o is 0, 1, 2 or 3;
Het is a heterocyclic 4- to 7-membered ring which may contain up to four N, O or S heteroatoms and wherein said heterocyclic 4- to 7-membered ring is optionally substituted by R7, R8 and R9, with the proviso that said heterocyclic 4- to 7-membered ring cannot be pyrrole; and
R7, R8, and R9 are each independently H, F, Cl, Br, $(C_1$–$C_6)$-alkyl, O—$(C_1$–$C_6)$-alkyl, O—$(C_2$–$C_6)$-alkenyl, O—$(C_2$–$C_6)$-alkynyl, OH, oxo, O—$(C_1$–$C_6)$-alkyl, $NH_2$, NH—$(C_1$–$C_6)$-alkyl, N—$[(C_1$–$C_6)$-alkyl$]_2$, COOH, CO—$(C_1$–$C_6)$-alkyl, COO—$(C_1$–$C_6)$-alkyl, $CONH_2$, CONH—$(C_1$–$C_6)$-alkyl, CON—$[(C_1$–$C_6)$-alkyl$]_2$, $(C_0$–$C_6)$-alkylene-aryl or $(C_1$–$C_6)$-alkylene-COO—$(C_1$–$C_6)$-alkyl, wherein said $(C_1$–$C_6)$-alkyl, O—$(C_1$–$C_6)$-alkyl, O—$(C_2$–$C_6)$-alkenyl, O—$(C_2$–$C_6)$-alkynyl, O—$(C_1$–$C_6)$-alkyl, NH—$(C_1$–$C_6)$-alkyl, N—$[(C_1$–$C_6)$-alkyl$]_2$, CO—$(C_1$–$C_6)$-alkyl, COO—$(C_1$–$C_6)$-alkyl, CONH—$(C_1$–$C_6)$-alkyl, CON—$[(C_1$–$C_6)$-alkyl$]_2$, $(C_0$–$C_6)$-alkylene-aryl and $(C_1$–$C_6)$-alkylene-COO—$(C_1$–$C_6)$-alkyl are optionally substituted by COOH, $CONH_2$, CONH—$(C_1$–$C_6)$-alkyl, CON—$[(C_1$–$C_6)$-alkyl$]_2$, OCO—$(C_1$–$C_6)$-alkyl, F, Cl, $(C_1$–$C_6)$-alkyl or O—$(C_1$–$C_6)$-alkyl;
and two radicals selected from said R7, R8 and R9 may optionally be bonded together to form a ring fused onto said heterocyclic 4- to 7-membered ring;
and pharmaceutically acceptable salts thereof.

Preference is given to compounds of the formula I where
R1 and R2 are H;
R3 and R4 are each independently F, Cl or Br;
R5 is H, F, Cl, Br, OH, $NO_2$, CN, $(C_1$–$C_6)$-alkyl, O—$(C_1$–$C_4)$-alkyl, CO—$(C_1$–$C_6)$-alkyl, $(C_0$–$C_6)$-alkylene-COOH, $(C_0$–$C_6)$-alkylene-COO—$(C_1$–$C_6)$-alkyl, $SO_2$—$(C_1$–$C_6)$-alkyl, O—$(C_2$–$C_6)$-alkenyl or $(C_2$–$C_6)$-alkynyl, wherein said $(C_1$–$C_6)$-alkyl, O—$(C_1$–$C_4)$-alkyl, CO—$(C_1$–$C_6)$-alkyl, $(C_0$–$C_6)$-alkylene-COOH, $(C_0$–$C_6)$-alkylene-COO—$(C_1$–$C_6)$-alkyl, $SO_2$—$(C_1$–$C_6)$-alkyl, O—$(C_2$–$C_6)$-alkenyl and $(C_2$–$C_6)$-alkynyl are optionally mono- or polysubstituted by F, Cl or Br;

A is H, F, Cl, Br, OH, $NO_2$, CN, $(C_1$–$C_6)$-alkyl, CO—$(C_1$–$C_6)$-alkyl, $(C_1$–$C_6)$-alkylene-COOH, $(C_1$–$C_6)$-alkylene-COO$(C_1$–$C_6)$-alkyl, $SO_2$—$(C_1$–$C_6)$-alkyl, $(C_2$–$C_6)$-alkenyl, $(C_2$–$C_6)$-alkynyl, O—$(C_1$–$C_6)$-alkyl, $S(O)_{1-2}$—

($C_1$–$C_6$)-alkyl-, NH—($C_1$–$C_6$)-alkyl, N—[($C_1$–$C_6$)-alkyl]$_2$, COOH, COO—($C_1$–$C_6$)-alkyl, CONH$_2$, CONH—($C_1$–$C_6$)-alkyl, CON—[($C_1$–$C_6$)-alkyl]$_2$, SO$_2$NH$_2$, SO$_2$NH—($C_1$–$C_6$)-alkyl, SO$_2$N—[($C_1$–$C_6$)-alkyl]$_2$ or NHCOR6, wherein said ($C_1$–$C_6$)-alkyl, CO—($C_1$–$C_6$)-alkyl, ($C_1$–$C_6$)-alkylene-COOH, ($C_1$–$C_6$)-alkylene-COO($C_1$–$C_6$)-alkyl, SO$_2$—($C_1$–$C_6$)-alkyl, ($C_2$–$C_6$)-alkenyl, ($C_2$–$C_6$)-alkynyl, O—($C_1$–$C_6$)-alkyl, S(O)$_{1-2}$—($C_1$–$C_6$)-alkyl-, NH—($C_1$–$C_6$)-alkyl, N—[($C_1$–$C_6$)-alkyl]$_2$, COO—($C_1$–$C_6$)-alkyl, CONH—($C_1$–$C_6$)-alkyl, CON—[($C_1$–$C_6$)-alkyl]$_2$, SO$_2$NH—($C_1$–$C_6$)-alkyl and SO$_2$N—[($C_1$–$C_6$)-alkyl]$_2$ are optionally mono- or polysubstituted by F, Cl, Br, COOH, COO—($C_1$–$C_6$)-alkyl, CONH$_2$, CONH—($C_1$–$C_6$)-alkyl, CON—[($C_1$–$C_6$)-alkyl]$_2$ or OCO—($C_1$–$C_6$)-alkyl;

R6 is H, ($C_1$–$C_6$)-alkyl, ($C_3$–$C_7$)-cycloalkyl, ($C_3$–$C_7$)-cycloalkyl-($C_1$–$C_4$)-alkylene, ($C_2$–$C_6$)-alkenyl, ($C_2$–$C_6$)-alkynyl, ($C_1$–$C_6$)-alkylene-COO—($C_1$–$C_6$)-alkyl, ($C_1$–$C_6$)-alkylene-CO—($C_1$–$C_6$)-alkyl, ($C_0$–$C_6$)-alkylene-COOH, ($C_1$–$C_6$)-alkylene-CONH$_2$, ($C_6$–$C_{10}$)-aryl, ($C_1$–$C_4$)-alkylene-($C_6$–$C_{10}$)-aryl, heteroaryl, ($C_1$–$C_4$)-alkylene-heteroaryl or CO-heteroaryl, wherein said ($C_1$–$C_6$)-alkyl, ($C_3$–$C_7$)-cycloalkyl, ($C_3$–$C_7$)-cycloalkyl-($C_1$–$C_4$)-alkylene, ($C_2$–$C_6$)-alkenyl, ($C_2$–$C_6$)-alkynyl, ($C_1$–$C_6$)-alkylene-COO—($C_1$–$C_6$)-alkyl, ($C_1$–$C_6$)-alkylene-CO—($C_1$–$C_6$)-alkyl, ($C_0$–$C_6$)-alkylene-COOH and ($C_1$–$C_6$)-alkylene-CONH$_2$ groups are optionally mono- or polysubstituted by F, Cl, Br, O—($C_1$–$C_4$)-alkyl, COO—($C_1$–$C_4$-alkyl), or N—[($C_1$–$C_4$)-alkyl]$_2$, and said ($C_6$–$C_{10}$)-aryl, ($C_1$–$C_4$)-alkylene-($C_6$–$C_{10}$)-aryl, heteroaryl, ($C_1$–$C_4$)-alkylene-heteroaryl and CO-heteroaryl are optionally mono- or polysubstituted by F, Cl, Br, NO$_2$, CN, O—($C_1$–$C_4$-alkyl), COO—($C_1$–$C_4$-alkyl), S—COO($C_1$–$C_4$-alkyl), N—[($C_1$–$C_4$)-alkyl]$_2$ or ($C_1$–$C_6$)-alkyl;

n is 0, 1 or 2;

m is 1;

o is 0 or 1;

Het is a heterocyclic 4- to 7-membered ring selected from triazolyl, tetrazolyl, oxadiazolyl, pyrazolyl, benzimidazolyl, furyl, triazinyl or

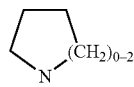

wherein said heterocyclic 4- to 7-membered ring is optionally substituted by R7, R8 and R9; and R7, R8, and R9 are each independently H, F, Cl, Br, ($C_1$–$C_6$)-alkyl, O—($C_1$–$C_6$)-alkyl, O—($C_2$–$C_6$)-alkenyl, O—($C_2$–$C_6$)-alkynyl, OH, oxo, O—($C_1$–$C_6$)-alkyl, NH$_2$, NH—($C_1$–$C_6$)-alkyl, N—[($C_1$–$C_6$)-alkyl]$_2$, COOH, CO—($C_1$–$C_6$)-alkyl, COO—($C_1$–$C_6$)-alkyl, CONH$_2$, CONH—($C_1$–$C_6$)-alkyl, CON—[($C_1$–$C_6$)-alkyl]$_2$, ($C_0$–$C_6$)-alkylene-aryl or ($C_1$–$C_6$)-alkylene-COO—($C_1$–$C_6$)-alkyl, wherein said ($C_1$–$C_6$)-alkyl, O—($C_1$–$C_6$)-alkyl, O—($C_2$–$C_6$)-alkenyl, O—($C_2$–$C_6$)-alkynyl, O—($C_1$–$C_6$)-alkyl, NH—($C_1$–$C_6$)-alkyl, N—[($C_1$–$C_6$)-alkyl]$_2$, CO—($C_1$–$C_6$)-alkyl, COO—($C_1$–$C_6$)-alkyl, CONH—($C_1$–$C_6$)-alkyl, CON—[($C_1$–$C_6$)-alkyl]$_2$, ($C_0$–$C_6$)-alkylene-aryl and ($C_1$–$C_6$)-alkylene-COO—($C_1$–$C_6$)-alkyl are optionally substituted by COOH, CONH$_2$, CONH—($C_1$–$C_6$)-alkyl, CON—[($C_1$–$C_6$)-alkyl]$_2$, OCO—($C_1$–$C_6$)-alkyl, F, Cl, ($C_1$–$C_6$)-alkyl or O—($C_1$–$C_6$)-alkyl;

and two radicals selected from said R7, R8 and R9 may optionally be bonded together to form a ring fused onto said heterocyclic 4- to 7-membered ring;

and pharmaceutically acceptable salts thereof.

Preference is furthermore given to the compounds of the formula I where

R1 and R2 are H;

R3 and R4 are each independently F, Cl or Br;

R5 is H, F, Cl, Br, OH, NO$_2$, CN, ($C_1$–$C_6$)-alkyl, O—($C_1$–$C_4$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl, SO$_2$—($C_1$–$C_6$)-alkyl, O—($C_2$–$C_6$)-alkenyl or ($C_2$–$C_6$)-alkynyl, wherein said ($C_1$–$C_6$)-alkyl, O—($C_1$–$C_4$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl, SO$_2$—($C_1$–$C_6$)-alkyl, O—($C_2$–$C_6$)-alkenyl and ($C_2$–$C_6$)-alkynyl are optionally mono- or polysubstituted by F, Cl or Br;

A is H, F, Cl, Br, ($C_1$–$C_6$)-alkyl, CF$_3$, OCF$_3$, NO$_2$, CN, O—($C_1$–$C_6$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl or SO$_2$—($C_1$–$C_6$)-alkyl;

n is 0, 1 or 2;

m is 1;

o is 0 or 1;

Het is a heterocyclic 4- to 7-membered ring group selected from triazolyl, tetrazolyl, oxadiazolyl, furyl, triazinyl or

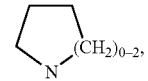

wherein said 4- to 7-membered heterocyclic ring is optionally substituted by R7, R8 and R9; and R7, R8, and R9 are each independently H, ($C_1$–$C_6$)-alkyl, OH, oxo, NH$_2$, COOH, COO—($C_1$–$C_6$)-alkyl, CONH$_2$, CONH—($C_1$–$C_6$)-alkyl or CON—[($C_1$–$C_6$)-alkyl]$_2$, wherein said ($C_1$–$C_6$)-alkyl, COO—($C_1$–$C_6$)-alkyl, CONH—($C_1$–$C_6$)-alkyl and CON—[($C_1$–$C_6$)-alkyl]$_2$ are optionally substituted by COOH;

and pharmaceutically acceptable salts thereof.

Very particular preference is given to compounds of the formula Ia

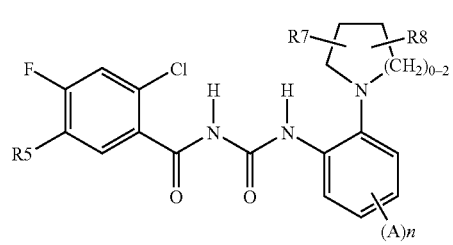

wherein

R5 is H, F, Cl, Br, ($C_1$–$C_6$)-alkyl, CF$_3$, OCF$_3$, NO$_2$, CN, O—($C_1$–$C_6$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl or SO$_2$—($C_1$–$C_6$)-alkyl;

A is H, F, Cl, Br, ($C_1$–$C_6$)-alkyl, CF$_3$, OCF$_3$, NO$_2$, CN, O—($C_1$–$C_6$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl or SO$_2$—($C_1$–$C_6$)-alkyl;

R7 is H, (C$_1$–C$_6$)-alkyl, (C$_0$–C$_6$)-alkylene-aryl, O—(C$_1$–C$_6$)-alkyl, O—(C$_2$–C$_6$)-alkenyl or O—(C$_2$–C$_6$)-alkynyl, wherein said (C$_1$–C$_6$)-alkyl, (C$_0$–C$_6$)-alkylene-aryl, O—(C$_1$–C$_6$)-alkyl, O—(C$_2$–C$_6$)-alkenyl and O—(C$_2$–C$_6$)-alkynyl are optionally mono- or polysubstituted by F, Cl or Br;
R8 is —(C=O)—X;
X is OH, O—(C$_1$–C$_6$)-alkyl, NH$_2$, NH—(C$_1$–C$_6$)-alkyl or N—[(C$_1$–C$_6$)-alkyl]$_2$; and
n is 1 or 2;

and pharmaceutically acceptable salts thereof.

Very particular preference is furthermore given to compounds of the formula Iaa,

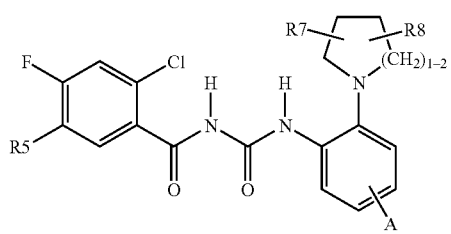

Iaa wherein
R5 is H or F;
A is H, F, Cl, (C$_1$–C$_6$)-alkyl, CF$_3$, COO—(C$_1$–C$_6$)-alkyl, COOH or SO$_2$—(C$_1$–C$_6$)-alkyl;
R7 is H or phenyl;
R8 is —(C=O)—X; and
X is OH, O—(C$_1$–C$_6$)-alkyl, NH$_2$, NH—(C$_1$–C$_6$)-alkyl or N—[(C$_1$–C$_6$)-alkyl]$_2$;

and pharmaceutically acceptable salts thereof.

The invention relates to compounds of the formula I, in the form of their racemates, racemic mixtures and pure enantiomers, and also to their diastereomers and mixtures thereof.

The alkyl radicals in the substituents A, R1, R2, R3, R4, R5, R6, R7, R8 and R9 may be either straight-chain or branched.

When radicals or substituents can occur more than once in the compounds of the formula I, they may each independently be defined as specified and be the same or different.

As a consequence of their higher water solubility compared to the starting or basic compounds, pharmaceutically acceptable salts are particularly suitable for medical applications. These salts have to have a pharmaceutically acceptable anion or cation. Suitable pharmaceutically acceptable acid addition salts of the compounds according to the invention are salts of inorganic acids such as hydrochloric acid, hydrobromic acid, phosphoric acid, metaphosphoric acid, nitric acid and sulfuric acid, and also organic acids, e.g. acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts having a pharmaceutically unacceptable anion, for example trifluoroacetate, are likewise encompassed by the scope of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I according to the invention, e.g. an ester which is able, on administration to a mammal, e.g. a human, to (directly or indirectly) form a compound of the formula I or an active metabolite thereof.

The physiologically functional derivatives also include prodrugs of the compounds according to the invention, for example as described in H. Okada et al., Chem. Pharm. Bull. 1994, 42, 57–61. Such prodrugs can be metabolized in vivo to a compound according to the invention. These prodrugs may or may not be active themselves.

The compounds according to the invention can also exist in different polymorphous forms, for example as amorphous and crystalline polymorphous forms. All polymorphous forms of the compounds according to the invention are encompassed by the scope of the invention and are a further aspect of the invention.

As used herein, the following definitions apply:

"Patient" means a warm blooded animal, such as for example rat, mice, dogs, cats, guinea pigs, and primates such as humans.

"Treat" or "treating" means to alleviate symptoms, eliminate the causation of the symptoms either on a temporary or permanent basis, or to prevent or slow the appearance of symptoms of the named disorder or condition.

"Therapeutically effective amount" means a quantity of the compound which is effective in treating the named disorder or condition.

"Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

"Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents and which in comparison to their free base forms, generally demonstrate higher melting points.

"Pharmaceutically acceptable basic addition salts" means non-toxic organic or inorganic basic addition salts of the compounds of Formula (I) or any of its intermediates.

Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

All references given below to "compound(s) of formula I" refer to compound(s) of the formula I as described above, and also to their salts, solvates and physiologically functional derivatives as described herein.

An aryl radical refers to a phenyl, naphthyl, biphenyl, tetrahydronaphthyl, alpha- or beta-tetralone, indanyl or indan-1-onyl radical.

The compound(s) of the formula (I) can also be administered in combination with further active ingredients.

The amount of a compound of formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg and 50 mg) per day per kilogram of bodyweight, for example 3–10 mg/kg/day. An intravenous dose may, for example, be in the range from 0.3 mg to 1.0 mg/kg and may advantageously be administered as an infusion of from 10 ng to 100 ng per kilogram per minute. Suitable infusion solutions for these purposes may, for example, contain from 0.1 ng to 10 mg, typically from 1 ng to 10 mg, per milliliter. Individual doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The support may be a solid or a liquid or both and is preferably formulated with the compound as a single dose, for example as a tablet, which may contain from 0.05 to 95% by weight of the active ingredient. Further pharmaceutically active substances may likewise be present, including further compounds of formula I. The pharmaceutical compositions according to the invention may be produced by one of the known pharmaceutical methods which consist essentially of mixing the ingredients with pharmacologically acceptable carriers and/or excipients.

Pharmaceutical compositions according to the invention are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a certain amount of the compound of formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are prepared by uniform and homogeneous mixing of the active ingredient with a liquid and/or finely divided solid carrier, after which the product is shaped if necessary. For example, a tablet can be produced by compressing or shaping a powder or granules of the compound, optionally with one or more additional ingredients. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain the compound of formula I with a flavoring, customarily sucrose, and gum arabic or tragacanth, and pastilles which include the compound in an inert base such as gelatin and glycerol or sucrose and gum arabic.

Suitable pharmaceutical compositions for parenteral administration include preferably sterile aqueous preparations of a compound of formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. The injectable compositions according to the invention generally contain from 0.1 to 5% by weight of the active compound.

Suitable pharmaceutical compositions for rectal administration are preferably in the form of single dose suppositories. These can be prepared by mixing a compound of formula I with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters advantageously contain the active ingredient in an optionally buffered aqueous solution, dissolved and/or dispersed in an adhesive or dispersed in a polymer. A suitable active ingredient concentration is from approx. 1% to 35%, preferably from approx. 3 to 15%. A particular means of releasing the active ingredient is by electrotransport or iontophoresis, as described, for example, in Pharmaceutical Research, 2(6): 318 (1986).

Further useful active ingredients for combination products are as follows: All antidiabetics mentioned in the Rote Liste 2001, chapter 12. They can be combined with the compounds of the formula I according to the invention, in particular for synergistic enhancement of the action. The active ingredient combination can be administered either by separately administering the active ingredients to the patient or in the form of combination products in which a plurality of active ingredients are present in one pharmaceutical preparation. Most of the active ingredients listed hereinbelow are disclosed in USP Dictionary of USAN and International Drug Names, US Pharmacopeia, Rockville 2001.

Antidiabetics include insulin and insulin derivatives, for example Lantus® (see www.lantus.com) or HMR 1964, fast-acting insulins (see U.S. Pat. No. 6,221,633), GLP-1 derivatives, for example those disclosed in WO 98/08871 of Novo Nordisk A/S, and orally active hypoglycemic active ingredients.

The orally active hypoglycemic active ingredients preferably include sulfonylureas, biguanidines, meglitinides, oxadiazolidinediones, thiazolidinediones, glucosidase inhibitors, glucagon antagonists, GLP-1 agonists, potassium channel openers, for example those disclosed in WO 97/26265 and WO 99/03861 of Novo Nordisk A/S, insulin sensitizers, inhibitors of liver enzymes which are involved in the stimulation of gluconeogenesis and/or glycogenolysis, modulators of glucose uptake, compounds which alter lipid metabolism such as antihyperlipidemic active ingredients and antilipidemic active ingredients, compounds which reduce food intake, PPAR and PXR agonists and active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin.

In another embodiment of the invention, the compounds of the formula I are administered in combination with a cholesterol absorption inhibitor, for example, ezetimibe, tiqueside, pamaqueside.

In another embodiment of the invention, the compounds of the formula I are administered in combination with a PPAR gamma agonist, for example, rosiglitazone, pioglitazone, JTT-501, GI 262570.

In another embodiment of the invention, the compounds of the formula I are administered in combination with PPAR alpha agonist, for example, GW 9578, GW 7647.

In another embodiment of the invention, the compounds of the formula I are administered in combination with a mixed PPAR alpha/gamma agonist, for example, GW 1536, AVE 8042, AVE 8134, AVE 0847, or as described in PCT/US 11833, PCT/US 11490, DE10142734.4.

In another embodiment of the invention, the compounds of the formula I are administered in combination with a fibrate, for example, fenofibrate, clofibrate, bezafibrate.

In another embodiment of the invention, the compounds of the formula I are administered in combination with an MTP inhibitor, for example, implitapide, BMS-201038, R-103757.

In another embodiment of the invention, the compounds of the formula I are administered in combination with bile acid absorption inhibitor (see, for example, U.S. Pat. No. 6,245,744 or U.S. Pat. No. 6,221,897), for example, HMR 1741.

In another embodiment of the invention, the compounds of the formula I are administered in combination with a CETP inhibitor, for example, JTT-705.

In another embodiment of the invention, the compounds of the formula I are administered in combination with a polymeric bile acid adsorbent, for example, cholestyramine, colesevelam.

In another embodiment of the invention, the compounds of the formula I are administered in combination with an LDL receptor inducer (see U.S. Pat. No. 6,342,512), for example, HMR1171, HMR1586.

In another embodiment of the invention, the compounds of the formula I are administered in combination with an ACAT inhibitor, for example, avasimibe.

In another embodiment of the invention, the compounds of the formula I are administered in combination with an antioxidant, for example, OPC-14117.

In another embodiment of the invention, the compounds of the formula I are administered in combination with a lipoprotein lipase inhibitor, for example, NO-1886.

In another embodiment of the invention, the compounds of the formula I are administered in combination with an ATP-citrate lyase inhibitor, for example, SB-204990.

In another embodiment of the invention, the compounds of the formula I are administered in combination with a squalene synthetase inhibitor, for example, BMS-188494.

In another embodiment of the invention, the compounds of the formula I are administered in combination with a lipoprotein(a) antagonist, for example, CI-1027 or nicotinic acid.

In another embodiment of the invention, the compounds of the formula I are administered in combination with a lipase inhibitor, for example, orlistat.

In another embodiment of the invention, the compounds of the formula I are administered in combination with insulin.

In another embodiment, the compounds of the formula I are administered in combination with a sulfonylurea, for example, tolbutamide, glibenclamide, glipizide or glimepiride.

In another embodiment, the compounds of the formula I are administered in combination with a biguanide, for example, metformin.

In another embodiment, the compounds of the formula I are administered in combination with a meglitinide, for example, repaglinide.

In another embodiment, the compounds of the formula I are administered in combination with a thiazolidinedione, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In another embodiment, the compounds of the formula I are administered in combination with an α-glucosidase inhibitor, for example, miglitol or acarbose.

In another embodiment, the compounds of the formula I are administered in combination with an active ingredient which acts on the ATP-dependent potassium channel of the beta cells, for example, tolbutamide, glibenclamide, glipizide, glimepiride or repaglinide.

In another embodiment, the compounds of the formula I are administered in combination with more than one of the abovementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In a further embodiment, the compounds of the formula I are administered in combination with CART modulators (see "Cocaine-amphetamine-regulated transcript influences energy metabolism, anxiety and gastric emptying in mice" Asakawa, A, et al., M.:Hormone and Metabolic Research (2001), 33(9), 554–558), NPY antagonists, e.g. naphthalene-1-sulfonic acid {4-[(4-aminoquinazolin-2-ylamino)methyl] cyclohexylmethyl}amide; hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxo-ethyl]amide; (WO 01/91752)), orexin antagonists (e.g. 1-(2-methylbenzoxazol-6-yl)-3-[1,5]naphthyridin-4-ylurea; hydrochlorides (SB-334867-A)), H3 agonists (3-cyclohexyl-1-(4,4-dimethyl-1,4,6,7-tetrahydroimidazo[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl] dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol; hydrochlorides (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525)); serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873–881), DA agonists (bromocriptine, Doprexin), lipase/amylase inhibitors (e.g. WO 00/40569), PPAR modulators (e.g. WO 00/78312), RXR modulators or TR-β agonists.

In another embodiment of the invention, the other active ingredient is leptin, see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615–1622.

In another embodiment, the other active ingredient is dexamphatamine or amphetamine.

In another embodiment, the other active ingredient is fenfluramine or dexfenfluramine.

In another embodiment, the other active ingredient is sibutramine.

In another embodiment, the other active ingredient is orlistat.

In another embodiment, the other active ingredient is mazindol or phentermine.

In yet another embodiment, the compounds of the formula I are administered in combination with dietary fiber materials, preferably insoluble dietary fiber materials (see, for example, Carob/Caromax® (Zunft H J; et al., Carob pulp preparation for treatment of hypercholesterolemia, ADVANCES IN THERAPY (2001 September-October), 18(5), 230–6.) Caromax is a carob-containing product supplied by Nutrinova, Nutrition Specialties & Food Ingredients GmbH, Industriepark Hochst, 65926 Frankfurt/Main)). Combination with Caromax® is possible in one preparation or by separate administration of compounds of the formula I and Caromax®. Caromax® can also be administered in the form of foodstuffs, for example, in bakery products or muesli bars.

It will be appreciated that any suitable combination of the compounds according to the invention with one or more of the abovementioned compounds and optionally one or more further pharmacologically active substances is regarded as being covered by the scope of protection of the present invention.

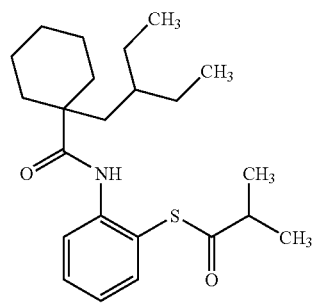

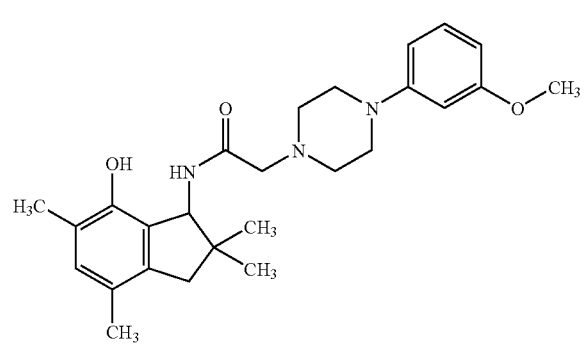

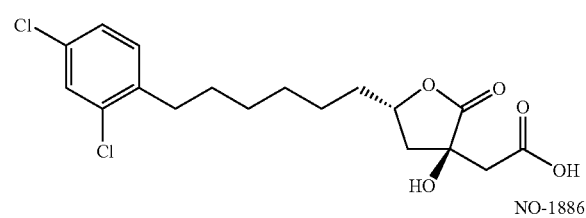

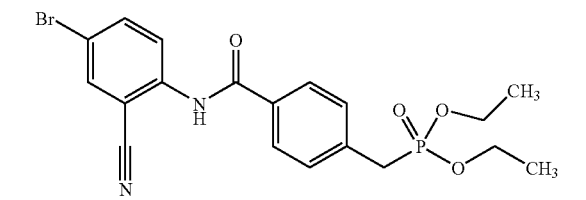

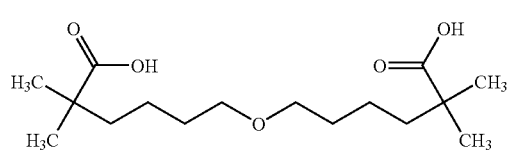

-continued

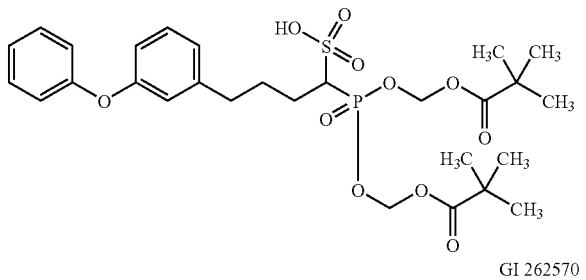

BMS-188494

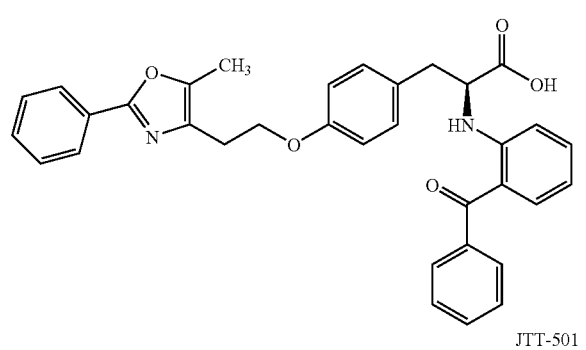

GI 262570

JTT-501

The contents of all references cited herein are hereby incorporated in their entirety by reference.

The above disclosure generally describes the present invention. A more complete understanding can be obtained by reference to the following specific examples which are provided herein for purposes of illustration only, and are not intended to limit the scope of the invention. The melting points and decomposition points (m.p.) measured were not corrected and are generally dependent upon the heating rate.

EXAMPLE 1 a) 1-(3-fluoro-4-nitrophenyl)-1H-[1,2,4]triazole

The mixture consisting of 2.5 g of 3-fluoro-4-nitrophenylhydrazine, 1.2 g of [1,2,3]triazine and 50 ml of ethanol was heated to reflux with stirring for 6 hours. After concentrating the reaction mixture under reduced pressure, the residue was worked up by column chromatography (solvent: 99:1 dichloromethane:methanol; silica gel).

| Yield: 0.8 g | m.p.: 99.9° C. | b) 1-(4-amino-3-fluorophenyl)-1H-[1,2,4]triazole

Hydrogen was introduced under atmospheric pressure into the mixture consisting of 260 mg of 1-(3-fluoro-4-nitrophenyl)-1H-[1,2,4]triazole, 30 mg of Pd/C and 30 ml of tetrahydrofuran until the theoretical amount had been taken up. After filtering off the catalyst with suction and concentrating the mixture under reduced pressure, the remaining oily residue was purified by column chromatography (solvent: 98:2 dichloromethane:methanol; silica gel).

| Yield: 100 mg | m.p.: 93.6° C. | c) 1-(2-chloro-4,5-difluorobenzoyl)-3-(2-fluoro-4-[1,2,4]triazol-1-yl phenyl)urea The solution of equivalent amounts of 2-chloro-4,5-difluorobenzoyl isocyanate was added dropwise to the solution of 75 mg of 1-(4-amino-3-fluorophenyl)-1H-[1,2,4]-triazole in 4 ml of acetonitrile and the mixture was stirred at room temperature for 30 minutes. The solid was filtered off with suction and dried under reduced pressure.

| Yield: 84 mg | m.p.: 195.0° C. |

EXAMPLE 2 a) 3-(3-methoxy-4-nitrophenyl)-5-methyl-4H-[1,2,4]triazole

The mixture consisting of 590 mg g of 3-methoxy-4-nitrobenzoic hydrazide, 6 ml of pyridine and 210 mg of thioacetamide was heated to 95° C. for 2 hours. After cooling, the volatile fractions were removed under reduced pressure at 40° C. and the residue was subjected to column chromatography purification (silica gel, solvent: 95:5 dichloromethane:methanol)

| Yield: 100 mg | m.p.: 176.0° C. | b) 2-methoxy-4-(5-methyl-4H-[1,2,4]triazol-3-yl)phenylamine was prepared by hydrogenating 100 mg of 3-(3-methoxy-4-nitrophenyl)-5-methyl-4H-[1,2,4]triazole in the presence of Pd/C in THF and used further without further purification.

| Yield: 110 mg (crude) | m.p.: 76.9° C. | c) 1-(2-chloro-4-fluorobenzoyl)-3-[2-methoxy-4-(5-methyl-4H-[1,2,4]triazol-3-yl)-phenyl]urea The solution of equivalent amounts of 2-chloro-4-fluorobenzoyl isocyanate was added dropwise to the solution of 35 mg of 2-methoxy-4-(5-methyl-4H-[1,2,4]triazol-3-yl) phenylamine in 3 ml of acetonitrile and the mixture was stirred at room temperature for 30 minutes. The solid was then filtered off with suction, stirred with t-butyl methyl ether, filtered off with suction and dried under reduced pressure.

| Yield: 33 mg | m.p.: 269.1° C. |

EXAMPLE 3

1-(2-chloro-4,5-difluorobenzoyl)-3-[2-methoxy-4-(5-methyl-4H-[1,2,4]triazol-3-yl)-phenyl]urea The solution of equivalent amounts of 2-chloro-4,5-difluorobenzoyl isocyanate was added dropwise to the solution of 30 mg of 2-methoxy-4-(5-methyl-4H-[1,2,4]triazol-3-yl)phenylamine in 3 ml of acetonitrile and the mixture was stirred at room temperature for 30 minutes. The solid was then filtered off with suction, stirred with isopropanol and dried under reduced pressure.

| Yield: 50 mg | m.p.: 227.5° C. |
|---|---|

EXAMPLE 4 a) ethyl [5-(3-methoxy-4-nitrophenyl)-4H-[1,2,4]triazol-3-yl]acetate 477 mg of malonic acid ethyl ester imidic acid ethyl ester hydrochloride were added to the solution of 633 mg of 3-methoxy-4-nitrobenzoic hydrazide in 2 ml of N-methylpyrrolidone and the mixture was heated to 140° C. for 3 hours. After cooling, the mixture was admixed with 50 ml of water and the product was extracted with ethyl acetate. After drying and concentrating the organic phase, it was purified by column chromatography (silica gel, solvent: 95:5 dichloromethane:methanol).

| Yield: 220 mg | m.p.: oil |
|---|---| b) ethyl [5-(4-amino-3-methoxyphenyl)-4H-[1,2,4]triazol-3-yl]acetate 50 mg of Pd/C were added to the solution of 200 mg of ethyl [5-(3-methoxy-4-nitrophenyl)-4H-[1,2,4]triazol-3-yl]acetate in 100 ml of ethanol and hydrogen was introduced into the mixture at room temperature until the theoretical amount had been taken up. The catalyst was then removed by filtration and the filtrate was concentrated.

| Yield: 140 mg | m.p.: oil |
|---|---| c) [5-(3-methoxy-4-nitrophenyl)-4H-[1,2,4]triazol-3-yl]acetic acid

The mixture of 140 mg of ethyl [5-(3-methoxy-4-nitrophenyl)-4H-[1,2,4]triazol-3-yl]acetate, 5 ml of methanol and 1 ml of 1N sodium hydroxide was stirred at room temperature for 2 hours. Afterwards, the volatile fractions are removed on a rotary evaporator, the residue is diluted with 10 ml of water and adjusted to pH 5 using 1N hydrochloric acid. The solid was filtered off with suction after the stirring.

| Yield: 99 mg | m.p.: 135.5° C. |
|---|---| d) (5-(4-(3-(2-chloro-4-fluorobenzoyl)ureido)-3-methoxyphenyl)-4H-[1,2,4]triazol-3-yl)acetic acid The solution of equivalent amounts of 2-chloro-4-fluorobenzoyl isocyanate in acetonitrile was added dropwise to the solution of 89 mg of [5-(3-methoxy-4-nitrophenyl)-4H-[1,2,4]triazol-3-yl]acetate in 5 ml of acetonitrile and the mixture was stirred at room temperature overnight. The solid formed was then filtered off with suction and dried under reduced pressure.

| Yield: 70 mg | m.p.: >300° C. (decomp.) |
|---|---|

EXAMPLE 5 a) 2-[3-methyl-5-(2-nitrophenyl)-[1,2,4]triazol-4-yl]benzoic acid

The mixture consisting of 1.8 g of 2-nitrobenzoic hydrazide, 1.6 g of 2-methylbenzo[d][1,3]oxazin-4-one and 5 ml of N-methylpyrrolidone was heated to 80° C. with stirring for 2 hours. After cooling, the mixture was admixed with water to slight cloudiness and stirred for a further 1 hour, during which time a solid precipitated out which was filtered off with suction, recrystallized from ethanol and dried under reduced pressure.

| Yield: 0.89 g | m.p.: 228.7° C. |
|---|---| b) 2-[3-methyl-5-(4-nitrophenyl)-[1,2,4]triazol-4-yl]benzoic acid was prepared correspondingly from 4-nitrobenzoic hydrazide and recrystallized from isopropanol.

| Yield: 0.6 g | m.p.: 275.4° C. |
|---|---| c) 2-[3-(2-aminophenyl)-5-methyl-[1,2,4]triazol-4-yl]benzoic acid was prepared by hydrogenating 400 mg of 2-[3-methyl-5-(2-nitrophenyl)-[1,2,4]triazol-4-yl]benzoic acid in the presence of Pd/C in tetrahydrofuran and purified by stirring with dichloromethane.

| Yield: 240 mg | m.p.: 179.4° C. |
|---|---| d) 2-[3-(4-aminophenyl)-5-methyl-[1,2,4]triazol-4-yl]benzoic acid was prepared by hydrogenating 270 mg of 2-[3-methyl-5-(4-nitrophenyl)-[1,2,4]triazol-4-yl]benzoic acid in the presence of Pd/C in tetrahydrofuran and purified by column chromatography (silica gel, solvent: 95:5 dichloromethane:methanol).

| Yield: 75 mg | m.p.: 207.8° C. |
|---|---| e) 2-(3-{2-[3-(2-chloro-4,5-difluorobenzoyl)ureido]phenyl}-5-methyl-[1,2,4]triazol-4-yl)benzoic acid The solution of equivalent amounts of 2-chloro-4-fluorobenzoyl isocyanate was added dropwise to the solution of 88 mg of 2-[3-(2-aminophenyl)-5-methyl-[1,2,4]triazol-4-yl]benzoic acid in 3 ml of acetonitrile and the mixture was stirred at room temperature for 30 minutes. The solid was filtered off with suction and dried under reduced pressure.

| Yield: 120 mg | m.p.: 194.7° C. |
|---|---|

EXAMPLE 6 a) 4-chloro-3-nitrobenzoic acid amidrazone hydrochloride

The mixture consisting of 6.8 g of ethyl 4-chloro-3-nitrobenzimidate hydrochloride, 100 ml of isopropanol and 3.75 ml of hydrazine hydrate was stirred at room temperature for 60 minutes. The precipitate was filtered off with suction and stirred briefly with 50 ml of isopropanol, filtered off with suction and dried under reduced pressure.

| Yield: 3.95 g | m.p.: 150.2° C. |
|---|---| b) 3-(4-chloro-3-nitrophenyl)-5-methyl-4H-[1,2,4]triazole

The mixture consisting of 322 mg of 4-chloro-3-nitrobenzoic acid amidrazone hydrochloride, 12 ml of toluene and 0.21 ml of trimethyl orthoacetate was heated to 110° C. for 60 minutes. The solvent was removed at 40° C. under reduced pressure and the residue purified by column chromatography (silica gel; 98:2 dichloromethane:methanol).

| Yield: 65 mg | m.p.: 167.9° C. |
|---|---| c) 3-(3-amino-4-chlorophenyl)-5-methyl-4H-[1,2,4]triazole

The mixture consisting of 120 mg of 3-(4-chloro-3-nitrophenyl)-5-methyl-4H-[1,2,4]triazole, 30 ml of ethyl acetate and 644 mg of tin chloride was heated to reflux for 6 hours. After cooling, the mixture was washed with water, and the organic phase was dried over sodium sulfate and concentrated at 40° C. under reduced pressure.

| Yield: 90 mg | m.p.: resin |
|---|---| d) 1-(2-chloro-4,5-difluorobenzoyl)-3-[2-chloro-5-(5-methyl-4H-[1,2,4]triazol-3-yl)phenyl]urea The solution of equivalent amounts of 2-chloro-4,5-difluorobenzoyl isocyanate was added dropwise to the solution of 85 mg of 3-(3-amino-4-chlorophenyl)-5-methyl-4H-1,2,4-triazole in 8 ml of acetonitrile and the mixture was stirred at room temperature for 2 hours. The solid formed is then filtered off with suction and dried under reduced pressure.

| Yield: 65 mg | m.p.: 227.4° C. |
|---|---|

In a similar manner, the following compounds were prepared:

e) 1-(2-chloro-4,5-difluorobenzoyl)-3-[2-chloro-5-(4H-[1,2,4]triazol-3-yl)phenyl]urea)

m.p.: 294.5° C.

f) 1-(2-chloro-4,5-difluorobenzoyl)-3-[2-trifluoromethoxy-4-(5-hydroxy-1H-[1,2,4]triazol-3-yl)phenyl]urea m.p.: >350° C.

EXAMPLE 7 a) 2-chloro-4-(1H-tetrazol-5-yl)phenylamine

The mixture consisting of 1.07 g of 4-amino-3-chlorobenzonitrile, 30 ml of xylene and 1.7 g of trimethyltin azide was stirred at 135° C. for 8 hours. After cooling, 25 ml of methanol were added, the mixture was stirred at room temperature for 30 minutes and the volatile constituents were removed on a rotary evaporator. On stirring, a solid precipitated out of the mixture obtained in this way, and was filtered off with suction and briefly dried under reduced pressure. This solid was dissolved in 1N sodium hydroxide solution and filtered, and the product was precipitated by acidifying with 2N hydrochloric acid, filtered off with suction and dried under reduced pressure.

| Yield: 1.24 g | m.p.: 183.8° C. |
|---|---| b) 4-(1H-tetrazol-5-yl)-2-trifluoromethoxyphenylamine was obtained in a similar manner from 505 mg of 4-amino-3-trifluoromethoxybenzonitrile.

| Yield: 360 mg | m.p.: 183.0° C. |
|---|---| c) 1-(2-chloro-4-fluorobenzoyl)-3-[2-chloro-4-(1H-tetrazol-5-yl)phenyl]urea

The solution of equivalent amounts of 2-chloro-4-fluorobenzoyl isocyanate was added dropwise to the solution of 100 mg of 2-chloro-4-(1H-tetrazol-5-yl)phenylamine in 3 ml of acetonitrile and the mixture was stirred at 40° C. for 60 minutes. The solid formed was filtered off with suction and dried under reduced pressure.

| Yield: 115 mg | m.p.: 227.6° C. |
|---|---| d) 1-(2-chloro-4,5-difluorobenzoyl)-3-[2-chloro-4-(1H-tetrazol-5-yl)phenyl)urea The solution of equivalent amounts of 2-chloro-4,5-difluorobenzoyl isocyanate was added dropwise to the solution of 100 mg of 2-chloro-4-(1H-tetrazol-5-yl)phenylamine in 3 ml of acetonitrile and the mixture was stirred at 40° C. for 60 minutes. The solid formed was filtered off with suction and dried under reduced pressure.

| Yield: 86 mg | m.p.: >300° C. |
|---|---| e) 1-(2-chloro-4-fluorobenzoyl)-3-[4-(1H-tetrazol-5-yl)-2-trifluoromethoxyphenyl]-urea was obtained in a similar manner from 100 mg of 5-(4-amino-3-trifluoromethoxyphenyl)tetrazole.

| Yield: 56 mg | m.p.: 276° C. |
|---|---| f) 1-(2-chloro-4,5-difluorobenzoyl)-3-[4-(1H-tetrazol-5-yl)-(2-trifluoromethoxy-phenyl]urea was obtained in a similar manner from 100 mg of 4-(1H-tetrazol-5-yl)-2-trifluoromethoxyphenylamine and 2-chloro-4,5-difluorobenzoyl isocyanate.

| Yield: 98 mg | m.p.: 215.0° C. |
|---|---|

EXAMPLE 8 a) 5-(3-methoxy-4-nitrophenyl)-3H-[1,3,4]oxadiazol-2-one 1.2 equivalents of a 20% phosgene solution in toluene were added dropwise to the solution of 850 mg of 3-methoxy-4-nitrobenzoic hydrazide (m.p.: 158.2° C., prepared from methyl 3-methoxy-4-nitrobenzoate and hydrazine hydrate in isopropanol at 80° C.) in 25 ml of dioxane and the mixture was stirred at room temperature for 1 hour. After concentrating, the residue was recrystallized from isopropanol, filtered off with suction and dried under reduced pressure.

| Yield: 620 mg | m.p.: 223.1° C. |
|---|---| b) [5-(4-amino-3-methoxyphenyl)-3H[1,3,4]oxadiazol-2-one

Hydrogen was introduced under atmospheric pressure into the mixture of 550 mg of 5-(3-methoxy-4-nitrophenyl)-3H-[1,3,4]oxadiazol-2-one, 100 mg of Pd/C and 50 ml of THF up to the theoretical uptake. Afterwards, the catalyst was filtered off with suction and the mixture was concentrated to dryness under reduced pressure.

| Yield: 500 mg | m.p.: 206.3° C. |
|---|---| c) 1-(2-chloro-4-fluorobenzoyl)-3-[4-(5-hydroxy-[1,3,4]oxadiazol-2-yl)-2-methoxyphenyl]urea The solution of equivalent amounts of 2-chloro-4-fluorobenzoyl isocyanate in acetonitrile was added dropwise to the solution of 103 mg of 25-(4-amino-3-methoxyphenyl)-3H-[1,3,4]oxadiazol-2-one in 5 ml of acetonitrile and the mixture was stirred at room temperature overnight. The solid formed was filtered off with suction and dried under reduced pressure.

| Yield: 155 mg | m.p.: 280.7° C. |
|---|---|

In a similar manner, the following compounds were prepared:

d) 1-(2-chloro-4-fluorobenzoyl)-3-[2-(5-hydroxy-[1,3,4]oxadiazol-2-yl)phenyl]urea m.p.:229.7° C.

e) 1-(2-chloro-4,5-difluorobenzoyl)-3-[4-(5-hydroxy-[1,3,4]oxadiazol-2-yl)-2-methoxyphenyl]urea m.p.: 293.1° C.

f) 1-(2-chloro-4,5-difluorobenzoyl)-3-[2-(5-hydroxy-[1,3,4]oxadiazol-2-yl)phenyl]urea m.p.:222.9° C.

g) 1-(2-chloro-4-fluorobenzoyl)-3-(2-[1,3,4]oxadiazol-2-ylphenyl)urea m.p.: 204.0° C.

h) 1-(2-chloro-4,5-difluorobenzoyl)-3-(2-[1,3,4]oxadiazol-2-ylphenyl)urea m.p.: 199.6° C.

EXAMPLE 9 a) 3-methoxy-4-nitrophenylhydrazine 4.5 ml of hydrazine hydrate were added dropwise to the solution of 3.2 g of 4-fluoro-2-methoxynitrobenzene in 15 ml of N-methylpyrolidone and the mixture was stirred for 2 hours, which initially resulted in gentle heating. The mixture was then diluted with 50 ml of water and stirred, and a precipitate formed which was filtered off with suction and dried under reduced pressure.

| Yield: 3.25 g | m.p.: 162.5° C. |
| --- | --- | b) methyl N'-(3-methoxy-4-nitrophenyl)hydrazinoformate 1.5 ml of methyl chloroformate were slowly added dropwise at room temperature to the solution of 3.0 g of 3-methoxy-4-nitrophenylhydrazine in 25 ml of dichloromethane and 6.6 ml of pyridine. After 2 hours, the volatile fractions were removed under reduced pressure on a rotary evaporator, the residue was taken up in water and, after weakly acidifying with 2N hydrochloric acid, extracted with ethyl acetate. After drying and concentrating the ethyl acetate phase, a solid residue remained which was recrystallized from isopropanol.

| Yield: 3.07 g | m.p.: 143.7° C. |
| --- | --- | c) 5-methoxy-3-(3-methoxy-4-nitrophenyl)-3H-[1,3,4]oxadiazol-2-one

The mixture consisting of 3.05 g of methyl N'-(3-methoxy-4-nitrophenyl)hydrazinoformate, 30 ml of dichloromethane, 5.2 ml of pyridine and 16.5 ml of a 20% toluenic phosgene solution was stirred at room temperature for 1 hour. After concentrating under reduced pressure, the semisolid residue was stirred with 50 ml of water with the addition of 3 ml of 2N hydrochloric acid, the solid was filtered off with suction and dried at RT under reduced pressure.

| Yield: 2.8 g | m.p.: 145.1° C. |
| --- | --- | d) 3-(4-amino-3-methoxyphenyl)-5-methoxy-3H-[1,3,4]oxadiazol-2-one hydrochloride Hydrogen was introduced at room temperature into the mixture consisting of 2.8 g of 5-methoxy-3-(3-methoxy-4-nitrophenyl)-3H-[1,3,4]oxadiazol-2-one, 250 ml of methanol and 0.3 g of Pd/C until the theoretical amount had been taken up. The catalyst was then removed by filtration and the filtrate was concentrated. The residue was taken up in ethyl acetate, the product was precipitated using methanolic hydrochloric acid, filtered off with suction and dried under reduced pressure.

| Yield: 2.0 g | m.p.: 245.9° C. |
| --- | --- | e) 1-(2-chloro-4-fluorobenzoyl)-3-(2-methoxy-4-(5-methoxy-2-oxo-3H-[1,3,4]-oxadiazol-3-yl)phenyl)urea The solution of equivalent amounts of 2-chloro-4-fluorobenzoyl isocyanate in acetonitrile was added dropwise to the solution of 0.39 g of 5-methoxy-3-(4-amino-3-methoxyphenyl)-3H-[1,3,4]oxadiazol-2-one hydrochloride and 0.2 ml of triethylamine in 5 ml of acetonitrile and the mixture is stirred at room temperature overnight. The solid formed was filtered off with suction and dried under reduced pressure.

| Yield: 0.16 g | m.p.: 211.1° C. |
| --- | --- |

In a similar manner, the following compound was prepared:

f) 1-(2-chloro-4-fluorobenzoyl)-3-(2-methyl-4-(5-methylamino-2-oxo-3H-[1,3,4]-oxadiazol-3-yl)phenyl)urea m.p.: 198.0° C.

g) 1-(2-chloro-4-fluorobenzoyl)-3-[2-chloro-4-(5-methyl-[1,3,4]oxadiazol-2-yl)phenyl]urea The mixture of 138 mg of 1-(2-chloro-4-fluorobenzoyl)-3-[2-chloro-4-(1H-tetrazol-5-yl)phenyl]urea, 180 mg of acetic anhydride, 260 mg of pyridine and 3 ml of dioxane was heated to 80° C. for 8 hours. After concentrating on a rotary evaporator under reduced pressure, the residue was stirred with water/glacial acetic acid, and the solid formed was filtered off with suction, dissolved in dichloromethane/methanol (1:1), and the solution was separated by filtration from the insoluble fraction. After concentrating under reduced pressure, the residue was stirred with ethanol and the solid was filtered off with suction.

| Yield: 11 mg | m.p.: 198.2° C. |
| --- | --- |

EXAMPLE 10 a) 5-(2-nitrophenyl)-[1,3,4]oxadiazol-2-ylamine 4 ml of a 5M cyanogen bromide solution in acetonitrile were added dropwise to the solution of 3.6 g of 2-nitrobenzoic hydrazide in 20 ml of acetonitrile. This resulted first in a clear solution, then a solid precipitated out which was filtered off with suction after continuing to stir for a short time, washed again with acetonitrile and dried under reduced pressure.

| Yield: 4.3 g | m.p.: 211.2° C. |
|---|---| b) 5-(2-aminophenyl)-[1,3,4]oxadiazol-2-ylamine

Hydrogen was introduced at atmospheric pressure into the solution of 350 mg of 5-(2-nitrophenyl)-[1,3,4]oxadiazol-2-ylamine until the theoretical amount had been taken up. After filtering off the catalyst with suction and concentrating the mixture under reduced pressure, the remaining oily residue was purified by column chromatography (solvent: 95:5 dichloromethane/methanol; silica gel).

| Yield: 200 mg | m.p.: 199.0° C. |
|---|---| c) 1-[2-(5-amino-[1,3,4]oxadiazol-2-yl)phenyl]-3-(2-chloro-4,5-difluorobenzoyl)urea The solution of equivalent amounts of 2-chloro-4-fluorobenzoyl isocyanate was added dropwise to the solution of 70 mg of 5-(2-aminophenyl)-[1,3,4]oxadiazol-2-ylamine in 2 ml of acetonitrile and the mixture was stirred at room temperature for 30 minutes. The solid was then filtered off with suction and dried under reduced pressure.

| Yield: 95 mg | m.p.: 205.8° C. |
|---|---|

EXAMPLE 11 a) N-[4-(N-hydroxycarbamimidoyl)-2-trifluoromethoxyphenyl]acetamide

The mixture consisting of 610 mg of N-(4-cyano-2-trifluoromethoxyphenyl)-acetamide, 15 ml of isopropanol, 255 mg of hydroxylamine hydrochloride and 410 mg of sodium acetate was heated to reflux for 5 hours. After cooling, the insoluble fraction was filtered off, and the filtrate is concentrated and taken up in a little isopropanol, the product was precipitated, filtered off with suction and dried by adding water until the first cloudiness and subsequent stirring.

| Yield: 280 mg | m.p.: 178.2° C. |
|---|---| b) N-[4-(5-oxo-4,5-dihydro-[1,2,4]oxadiazol-3-yl)-2-trifluoromethoxyphenyl]-acetamide The mixture consisting of 130 mg of N-[4-(N-hydroxycarbamimidoyl)-2-trifluoromethoxyphenyl]acetamide, 2 ml of N-methylpyrrolidone, 0.55 ml of pyridine and 0.049 ml of ethyl chloroformate was stirred at 80° C. for 5 hours. After cooling, the mixture was diluted with water and the product was extracted with 20 ml of ethyl acetate. The organic phase was dried over sodium sulfate and evaporated at 40° C. under reduced pressure.

| Yield: 200 mg | m.p.: resin |
|---|---| c) 3-(4-amino-3-trifluoromethoxyphenyl)-4H-[1,2,4]-oxadiazol-5-one hydrochloride The mixture consisting of 200 mg of N-[4-(5-oxo-4,5-dihydro-[1,2,4]oxadiazol-3-yl)-2-trifluoromethoxyphenyl]acetamide, 10 ml of methanol and 0.5 ml of a 4M solution of hydrochloric acid in dioxane was stirred at room temperature for 15 hours. After concentrating the volatile fractions on a rotary evaporator, a yellowish oil remains.

| Yield: 190 mg | m.p.: oil |
|---|---| d) 1-(2-chloro-4,5-difluorobenzoyl)-3-[4-(5-oxo-4,5-dihydro-[1,2,4]oxadiazol-3-yl)-2-trifluoromethoxyphenyl]urea The solution of equivalent amounts of 2-chloro-4,5-difluorobenzoyl isocyanate was added dropwise to the solution of 95 mg of 3-(4-amino-3-trifluoromethoxyphenyl)-4H-[1,2,4]-oxadiazol-5-one hydrochloride and 0.054 ml of Hünig's base in 4 ml of acetonitrile and the mixture was stirred at room temperature for 30 minutes. The solid was then filtered off with suction and dried under reduced pressure.

| Yield: 55 mg | m.p.: 224.5° C. |
|---|---|

In a similar manner, the following examples were prepared:

e) 1-(2-chloro-4-fluorobenzoyl)-3-[4-(5-oxo-4,5-dihydro-[1,2,4]oxadiazol-3-yl)-2-trifluoromethoxyphenyl]urea m.p. 230.1° C.

f) 1-(2-chloro-4-fluorobenzoyl)-3-[2-chloro-4-(5-oxo-4,5-dihydro-[1,2,4]oxadiazol-3-yl)phenyl]urea m.p. 243.6° C.

EXAMPLE 12 a) 5-methyl-2-(3-methyl-4-nitrophenyl)-1,2-dihydropyrazol-3-one

The mixture of 500 mg of 3-methyl-4-nitrophenylhydrazine, 0.32 ml of methyl acetoacetate and 20 ml of toluene was heated to 100° C. for 8 hours. After cooling, the reaction mixture was concentrated under reduced pressure and the residue was stirred in t-butyl methyl ether. The solid was filtered off with suction and dried under reduced pressure.

| Yield: 380 mg | m.p.: 179.0° C. |
|---|---| b) 2-(4-amino-3-methylphenyl)-5-methyl-1,2-dihydropyrazol-3-one

Hydrogen was introduced under atmospheric pressure into the mixture of 350 mg of 5-methyl-2-(3-methyl-4-nitrophenyl)-1,2-dihydropyrazol-3-one, 70 mg of Pd/C and 50 ml of tetrahydrofuran until the theoretical uptake. Afterwards, the catalyst was filtered off with suction and the mixture was concentrated to dryness under reduced pressure and the residue was stirred in t-butyl methyl ether. The solid was filtered off with suction and dried under reduced pressure.

| Yield: 280 mg | m.p.: 59.3° C. |
|---|---| c) 1-(2-chloro-4-fluorobenzoyl)-3-[2-methyl-4-(3-methyl-5-oxo-2,5-dihydropyrazol-1-yl)phenyl]urea The solution of equivalent amounts of 2-chloro-4-fluorobenzoyl isocyanate in acetonitrile was added dropwise to the solution of 71 mg of 2-(4-amino-3-methylphenyl)-5-methyl-1,2-dihydropyrazol-3-one in 6 ml of acetonitrile and the mixture was stirred at room temperature overnight. The solid formed was filtered off with suction and dried under reduced pressure.

| Yield: 70 mg | m.p.: 225.5° C. |
|---|---|

EXAMPLE 13 a) 1-[2-(1H-benzoimidazol-2-yl)phenyl]-3-(2-chloro-4,5-difluorobenzoyl)urea

The solution of equivalent amounts of 2-chloro-4,5-difluorobenzoyl isocyanate was added dropwise to the solution of 142 mg of 2-(1H-benzoimidazol-2-yl)phenylamine in 8 ml of acetonitrile and the mixture was stirred at room temperature for 30 minutes. The solid was then filtered off with suction and dried under reduced pressure.

| Yield: 250 mg | m.p.: 268° C. (decomp.) |
|---|---|

In a similar manner, the following compounds were prepared:

b) 5-{2-[3-(2-chloro-4,5-difluorobenzoyl)ureido]phenyl}furan-2-carboxylic acid m.p. 239.3° C.

c) 5-{2-[3-(2-chloro-4-fluorobenzoyl)ureido]phenyl}furan-2-carboxylic acid m.p. 236.3° C.

EXAMPLE 14 a) 3-(4-chloro-3-nitrophenyl)-6-methyl-4H-[1,2,4]triazin-5-one

The mixture consisting of 322 mg of 4-chloro-3-nitrobenzoic acid amidrazone hydrochloride, 12 ml of ethanol and 0.18 ml of ethyl pyruvate was heated to 80° C. for 60 minutes. After cooling, the precipitate was filtered off with suction, washed with a little ethanol and dried under reduced pressure at 40° C.

| Yield: 115 mg | m.p.: 247.1° C. |
|---|---| b) 3-(4-chloro-3-nitrophenyl)-5,6-dimethyl-[1,2,4]triazines

This compound was obtained in a similar manner to the above example starting from 2,3-butanedione.
m.p.: 167.7° C.

c) 3-(3-amino-4-chlorophenyl)-6-methyl-4H-[1,2,4]triazin-5-one

This compound was obtained by reducing 3-(4-chloro-3-nitrophenyl)-6-methyl-4H-[1,2,4]triazin-5-one with tin chloride.
m.p.: 258.1° C.

d) 2-chloro-5-(5,6-dimethyl-[1,2,4]triazin-3-yl)phenylamine

This compound was obtained by reducing 3-(4-chloro-3-nitrophenyl)-5,6-dimethyl-[1,2,4]triazine with tin chloride.
m.p.: 211.8° C.

e) 1-(2-chloro-4,5-difluorobenzoyl)-3-[2-chloro-5-(6-methyl-5-oxo-4,5-dihydro-[1,2,4]triazin-3-yl)phenyl]urea The solution of equivalent amounts of 2-chloro-4,5-difluorobenzoyl isocyanate was added dropwise to the solution of 60 mg of 3-(3-amino-4-chlorophenyl)-6-methyl-4H-[1,2,4]triazin-5-one in 8 ml of acetonitrile and the mixture was stirred at room temperature for 30 minutes. The solid was filtered off with suction and dried under reduced pressure.

| Yield: 75 mg | m.p.: 236.6° C. |
|---|---| f) 1-(2-chloro-4,5-difluorobenzoyl)-3-[2-chloro-5-(5,6-dimethyl-[1,2,4]triazin-3-yl)phenyl]urea The solution of equivalent amounts of 2-chloro-4,5-difluorobenzoyl isocyanate was added dropwise to the solution of 75 mg of 2-chloro-5-(5,6-dimethyl-[1,2,4]triazin-3-yl)phenylamine in 8 ml of acetonitrile and the mixture was stirred at room temperature for 30 minutes. The solid was filtered off with suction and dried under reduced pressure.

| Yield: 105 mg | m.p.: 229.2° C. |
|---|---|

EXAMPLE 15 a) 1-(4-fluoro-2-nitrophenyl)piperidine-3-carboxamide

The mixture consisting of 1.62 g of 2,5-difluoronitrobenzene, 1.9 g of nipecotamide and 10 ml of NMP was heated with stirring to 80° C. for 2 hours. After the mixture had been allowed to cool, 30 ml of water were added and the mixture was stirred at RT for 30 minutes. The precipitated solid was filtered off with suction and dried under reduced pressure.

| Yield: 2.8 g | m.p.: 142.5° C. |
|---|---| b) 1-(2-amino-4-fluorophenyl)piperidine-3-carboxamide hydrochloride

The solution of 2.67 g of 1-(4-fluoro-2-nitrophenyl)piperidine-3-carboxamide in 100 ml of THF was admixed with 260 mg of Pd/C. This mixture was hydrogenated in a shaking vessel at atmospheric pressure until the theoretical amount of hydrogen had been taken up. The mixture is then acidified with hydrogen chloride dissolved in ethyl acetate, the solid is filtered off with suction and washed with methanol, and the filtrate is concentrated under reduced pressure. The residue is triturated with tert-butyl methyl ether and the solid is filtered off with suction and dried under reduced pressure.

| Yield: 2.45 g | m.p. 159.2° C. |
|---|---| c) 1-{2-[3-(2-chloro-4,5-difluorobenzoyl)ureido]-4-fluorophenyl}piperidine-3-carboxamide The equimolar solution of 2-chloro-4,5-difluorobenzoyl isocyanate in acetonitrile was added dropwise to the solution of 109 mg of 1-(2-amino-4-fluorophenyl)piperidine-3-carboxamide hydrochloride in 5 ml of acetonitrile with stirring. The mixture was stirred at RT for 6 h and the precipitate was filtered off with suction and dried at RT under reduced pressure.

| Yield: 150 mg | m.p.: 216.0° C. |
|---|---|

EXAMPLE 16 a) 1-(4-fluoro-2-nitrophenyl)piperidine-4-carboxylic acid

The mixture consisting of 1.62 g of 2,5-difluoronitrobenzene, 1.9 g of piperidine-4-carboxylic acid and 10 ml of NMP was heated with stirring to 80° C. for 2 hours. After it had been allowed to cool, 30 ml of water were added and the mixture was made weakly acidic using 2N hydrochloric acid and stirred at RT. The precipitated solid was filtered off with suction and dried under reduced pressure.

| Yield: 3.4 g | m.p.: 143.7° C. |
|---|---| b) 1-(2-amino-4-fluorophenyl)piperidine-4-carboxylic acid hydrochloride

The solution of 804 mg of 1-(4-fluoro-2-nitrophenyl)piperidine-4-carboxylic acid in 40 ml of ethyl acetate was admixed with 3.8 g of tin(II) chloride and stirred at RT for 2 hours. 50 ml of water were then added and the mixture was filtered through a clarifying layer. The ethyl acetate phase was removed, dried over sodium sulfate and concentrated by rotary evaporator, leaving a semisolid residue which was subjected directly to further reaction.

| Yield: 395 mg | m.p.: crude product |
|---|---| c) 1-{2-[3-(2-chloro-4,5-difluorobenzoyl)ureido]-4-fluorophenyl}piperidine-4-carboxylic acid The equimolar solution of 2-chloro-4,5-difluorobenzoyl isocyanate in acetonitrile was added dropwise to the solution of 53 mg of 1-(2-amino-4-fluorophenyl)piperidine-4-carboxylic acid hydrochloride in 3 ml of acetonitrile with stirring. The mixture was stirred at RT for 6 h and the precipitate was filtered off with suction and dried at RT under reduced pressure.

| Yield: 75 mg | m.p.: 215.9° C. |
|---|---|

EXAMPLE 39 c) 1-{2-[3-(2-chloro-4,5-difluorobenzoyl)ureido]-4-fluorophenyl}piperidine-4-carboxylic acid sodium salt The solution of 100 mg of 1-{2-[3-(2-chloro-4,5-difluorobenzoyl)ureido]-4-fluoro-phenyl}piperidine-4-carboxylic acid in 8 ml of isopropanol at 60° C. is admixed with the equimolar amount of 2N sodium hydroxide solution and, after the addition of 20 ml of water, cooled slowly with stirring. The precipitated product is filtered off with suction, washed with isopropanol and water and dried under reduced pressure.

Yield: 85 mg   m.p. 160° C. (decomp.)

EXAMPLE 41 c) 1-{2-[3-(2-chloro-4,5-difluorobenzoyl)ureido]-4-chlorophenyl}piperidine-4-carboxylic acid The mixture consisting of 90 mg of methyl 1-{2-[3-(2-chloro-4,5-difluoro-benzoyl)ureido]-4-chlorophenyl}piperidine-4-carboxylate (Ex.15), 9.6 mg of lithium hydroxide, 3 ml of water, 3 ml of methanol and 3 ml of THF is allowed to stand at room temperature for 36 hours. The volatile fractions are removed at RT under reduced pressure and the remainder is adjusted to pH=4 using 2N hydrochloric acid. The precipitate formed is filtered off with suction and purified by column chromatography (silica gel, solvent: methylene chloride:methanol=9:1).

Yield: 30 mg   m.p.: resin

The compounds of the formula I can be prepared by reacting ureas of the formula 2 with reactive acid derivatives (formula 4) such as, for example, with acid chlorides or with anhydrides. Alternatively, the compounds of the formula I can be prepared by reacting aniline derivatives of the formula 3 with aroyl isocyanates.

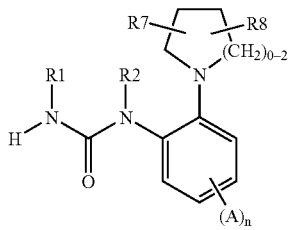

2

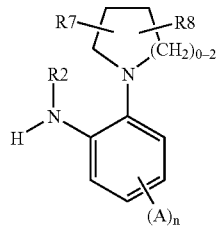

3

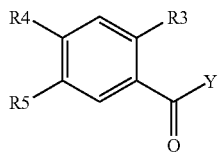

4 wherein R1, R2, R3, R4, R5, R7, R8, A, n and Y are each as defined above in formula I. If the compound of formula 4 is an acid chloride, Y is a chloride atom. If the compound of formula 4 is an isocyanate, Y is the group —N=C=O. If the compound of formula 4 is an anhydride, Y is a group of formula:

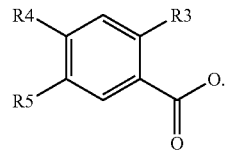

TABLE I

Compounds of the formula I

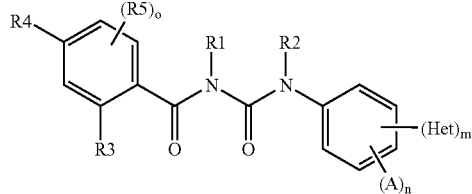

| Ex. | R1 | R2 | R3 | R4 | (R5)$_o$ | (A)$_n$ | (Het)$_m$ |
|---|---|---|---|---|---|---|---|
| 1c | H | H | Cl | F | 5-F | 2-fluoro | 4-((1,2,4)-triazol-1-yl) |
| 2c | H | H | Cl | F | H | 2-OMe | 4-(5-methyl-4H-(1,2,4)-triazol-3-yl) |
| 3 | H | H | Cl | F | 5-F | 2-OMe | 4-(5-methyl-4H-(1,2,4)-triazol-3-yl) |
| 4d | H | H | Cl | F | H | 2-OMe | 4-(1,2,4-triazole-3-acetic acid-5-yl) |
| 5e | H | H | Cl | F | 5-F | —H | 2-(5-methyl-4-(2-carboxyphenyl)-4H-[1,2,4]-triazol-3-yl) |
| 6d | H | H | Cl | F | 5-F | 2-chloro | 5-(5-methyl-(1,2,4)-triazol-3-yl) |
| 6e | H | H | Cl | F | 5-F | 2-chloro | 3-(4H-(1,2,4)-triazol-3-yl) |
| 6f | H | H | Cl | F | 5-F | 2-OCF$_3$ | 4-(5-hydroxy-1-H-(1,2,4)-triazol-3-yl) |
| 7c | H | H | Cl | F | H | 2-chloro | 4-(1H-tetrazol-5-yl) |
| 7d | H | H | Cl | F | 5-F | 2-chloro | 4-(1H-tetrazol-5-yl) |
| 7e | H | H | Cl | F | H | 2-OCF$_3$ | 4-(1H-tetrazol-5-yl) |
| 7f | H | H | Cl | F | 5-F | 2-OCF$_3$ | 4-(1H-tetrazol-5-yl) |
| 8c | H | H | Cl | F | H | 2-OMe | 4-(5-hydroxy-(1,3,4)-oxadiazol-2-yl) |
| 8d | H | H | Cl | F | H | —H | 2-(5-hydroxy-(1,3,4)-oxadiazol-2-yl) |
| 8e | H | H | Cl | F | 5-F | 2-OMe | 4-(5-hydroxy-(1,3,4)-oxadiazol-2-yl) |
| 8f | H | H | Cl | F | 5-F | —H | 2-(5-hydroxy-(1,3,4)-oxadiazol-2-yl) |
| 8g | H | H | Cl | F | H | —H | 2-(1,3,4-oxadiazol-2-yl) |
| 8h | H | H | Cl | F | 5-F | —H | 2-(1,3,4-oxadiazol-2-yl) |
| 9e | H | H | Cl | F | H | 2-OMe | 4-(5-methoxy-2-oxo-1,3,4-oxadiazol-3-yl) |
| 9f | H | H | Cl | F | H | 2-Me | 4-(5-methylamino-2-oxo-1,3,4-oxadiazol-3-yl) |
| 9g | H | H | Cl | F | H | 2-chloro | 4-(5-methyl-1,3,4-oxadiazol-2-yl) |
| 10c | H | H | Cl | F | 5-F | —H | 2-(5-amino-1,3,4-oxadiazol-2-yl) |
| 11d | H | H | Cl | F | 5-F | 2-OCF$_3$ | 4-(5-oxo-4,5-dihydro-(1,2,4)-oxadiazol-3-yl) |
| 11e | H | H | Cl | F | H | 2-OCF$_3$ | 4-(5-oxo-4,5-dihydro-(1,2,4)-oxadiazol-3-yl) |
| 11f | H | H | Cl | F | H | —Cl | 4-(5-oxo-4,5-dihydro-(1,2,4)-oxadiazol-3-yl) |
| 12c | H | H | Cl | F | H | 2-Me | 4-(3-methyl-5-oxo-pyrazol-1-yl) |
| 13a | H | H | Cl | F | 5-F | —H | 2-(benzimidazol-2-yl) |
| 13b | H | H | Cl | F | 5-F | —H | 2-(5-carboxyfur-2-yl) |
| 13c | H | H | Cl | F | H | —H | 2-(5-carboxyfur-2-yl) |
| 14e | H | H | Cl | F | 5-F | 2-chloro | 5-(6-methyl-5-oxo-4H-(1,2,4)-triazin-3-yl) |
| 14f | H | H | Cl | F | 5-F | 2-chloro | 5-(5,6-dimethyl-(1,2,4)-triazin-3-yl) |

TABLE II

Compounds of the formula Ia

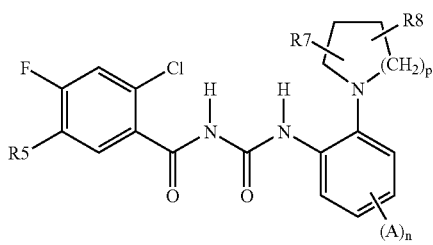

| Ex. | R5 | (A)n | R7 | (A)n | R8 | p | m.p. |
|---|---|---|---|---|---|---|---|
| 15 | F | 5-F | H | H | 3-CONH₂ | 2 | 216.0 |
| 16 | F | 5-F | H | H | 4-COOH | 2 | 221.7 |
| 17 | F | 5-F | H | H | 3-COOH | 2 | 184.2 |
| 18 | H | 5-F | H | H | 3-COOH | 2 | 205.6 |
| 19 | H | 5-F | H | H | 3-CONH₂ | 2 | 205.0 |
| 20 | H | 5-F | H | H | 4-COOH | 2 | 230.7 |
| 21 | F | 5-SO₂Me | H | H | 3-COOH | 2 | resin |
| 22 | H | 5-SO₂Me | H | H | 3-COOH | 2 | resin |
| 23 | F | 5-CF₃ | H | H | 3-COOH | 2 | resin |
| 24 | H | 5-CF₃ | H | H | 3-COOH | 2 | resin |
| 25 | H | 4-Me | H | H | 3-COOH | 2 | 188.4 |
| 26 | F | 4-Me | H | H | 3-COOH | 2 | 184.9 |
| 27 | F | 5-Me | H | H | 3-COOH | 2 | 219.4 |
| 28 | H | 5-Me | H | H | 3-COOH | 2 | 228.3 |
| 29 | F | 5-Cl | H | H | 4-COOMe | 2 | 206.6 |
| 30 | H | 5-Cl | H | H | 4-COOMe | 2 | 211.2 |
| 31 | F | 5-Cl | H | H | 3-COOH | 2 | 203.6 |
| 32 | H | 5-Cl | H | H | 3-COOH | 2 | 215.8 |
| 33 | F | 5-COOMe | H | H | 3-COOH | 2 | 227.3 |
| 34 | H | 5-COOMe | H | H | 3-COOH | 2 | 219.4 |
| 35 | F | 5-F | H | H | 3-COOEt | 2 | oil |
| 36 | H | 5-F | H | H | 3-COOEt | 2 | 145.2 |
| 37 | F | 5-F | H | H | 3-CONEt₂ | 2 | oil |
| 38 | H | 5-F | H | H | 3-CONEt₂ | 2 | 178.2 |
| 39 | F | 5-F | H | H | 4-COOMe | 2 | 207.0 |
| 40 | H | 5-F | H | H | 4-COOMe | 2 | 187.2 |
| 41 | F | 5-COOMe | H | H | 4-COOMe | 2 | 221.1 |
| 42 | H | 5-COOMe | H | H | 4-COOMe | 2 | 205.3 |
| 43 | H | 5-CF₃ | H | H | 4-COOH | 2 | 219.9 |
| 44 | F | 5-SO₂Me | H | H | 4-COOMe | 2 | 231.5 |
| 45 | H | 5-SO₂Me | H | H | 4-COOMe | 2 | 228.2 |
| 46 | H | 5-CF₃ | H | H | 4-COOH | 2 | 206.3 |
| 47 | F | 5-CF₃ | H | H | 4-COOMe | 2 | resin |
| 48 | F | H | H | H | 3-COOH | 1 | resin |
| 49 | H | 5-CF₃ | H | H | 4-COOMe | 2 | resin |
| 50 | F | 5-COOH | H | H | 3-COOH | 2 | 198.4 |
| 51 | F | 5-F | 4-phenyl | H | 4-COOH | 2 | 241.6 |
| 52 | F | 4-COOH | H | H | 4-COOMe | 2 | 238.6 |
| 53 | F | 4-F | H | H | 4-COONa | 2 | 160.9 |
| 54 | F | H | H | H | 4-COOH | 2 | 221.6 |
| 55 | F | 5-Cl | H | H | 4-COOH | 2 | resin |
| 56 | H | H | H | H | 4-COOH | 2 | 227.4 |
| 57 | F | 5-F | H | H | 4-COOH(tris salt) | 2 | 180.6 |
| 58 | F | 5-CF₃ | H | H | 3-COOEt | 2 | 184.6 |
| 59 | F | 5-F | 4-phenyl | H | 4-COOMe | 2 | 218.2 |
| 60 | F | 5-F | 4-phenyl | H | 4-CONH₂ | 2 | 236.4 |

The compounds of the formula I are notable for favorable effects on the lipid and carbohydrate metabolism, and in particular they reduce the blood sugar level and are suitable for treating type 2 diabetes, insulin resistance, dyslipidemias and the metabolic syndrome "syndrome X". The compounds are also suitable for prophylaxis and treatment of arteriosclerotic symptoms. The compounds may be used alone or in combination with further blood sugar-reducing active ingredients.

The effectiveness of the compounds was tested as follows:

Glycogen Phophorylase a Activity Test

The effect of compounds on the activity of the active form of glycogen phosphorylase (GPa) was measured in the reverse direction by monitoring the synthesis of glycogen from glucose 1-phosphate by determining the release of inorganic phosphate. All reactions were carried out as duplicate determinations in 96-well microtiter plates (half area plates, Costar No. 3696), and the change in absorption as a consequence of the formation of the reaction product was measured at the wavelength specified below in a Multiskan Ascent Elisa Reader (Lab Systems, Finland).

In order to measure the GPa enzyme activity in the reverse direction, the conversion of glucose 1-phosphate to glycogen and inorganic phosphate was measured by the general method of Engers et al. (Engers H D, Shechosky S, Madsen N B, Can J Biochem 1970 July;48(7):746–754) with the following modifications: human glycogen phosphorylase a (for example containing 0.76 mg of protein/ml (Aventis Pharma Deutschland GmbH), dissolved in buffer solution E (25 mM β-glycerophosphate, pH 7.0, 1 mM EDTA and 1 mM dithiothreitol) was diluted to a concentration of 10 μg of protein/ml with buffer T (50 mM Hepes, pH 7.0, 100 mM KCl, 2.5 mM EDTA, 2.5 mM MgCl₂6H₂O) and addition of 5 mg/ml of glycogen. Test substances were prepared as a 10 mM solution in DMSO and diluted to 50 μM with buffer solution T. To 10 μl of this solution were added 10 μl of 37.5 mM glucose dissolved in buffer solution T and 5 mg/ml of glycogen, and also 10 μl of a solution of human glycogen phosphorylase a (10 μg of protein/ml) and 20 μl of 2.5 mM glucose 1-phosphate. The base value of the activity of glycogen phosphorylase a in the absence of test substance was determined by adding 10 μl of buffer solution T (0.1% DMSO). The mixture was incubated at room temperature for 40 minutes and the released inorganic phosphate was determined by means of the general method of Drueckes et al. (al (Drueckes P, Schinzel R, Palm D, *Anal Biochem* 1995 Sep. 1;230(1):173–177) with the following modifications: 50 μl of a stop solution of 7.3 mM of ammonium molybdate, 10.9 mM of zinc acetate, 3.6% of ascorbic acid, 0.9% of SDS are added to 50 μl of the enzyme mixture. After 60 minutes of incubation at 45° C., the absorption was measured at 820 nm. To determine the background absorption, the stop solution was added immediately after the addition of the glucose 1-phosphate solution in a separate reaction. This test was carried out at a concentration of 10 μM of the test substance, in order to determine the respective inhibition of glycogen phosphorylase a by the test substance in vitro.

TABLE 2

Biological activity

| Ex. | % inhibition at 10 μM |
|---|---|
| 1c | 94 |
| 2c | 94 |
| 3 | 100 |
| 4d | 90 |
| 5e | 9 |
| 6d | 100 |
| 6e | 100 |
| 6f | 98 |
| 7c | 100 |
| 7d | 100 |
| 7e | 100 |
| 7f | 100 |
| 8c | 96 |
| 8d | 100 |

TABLE 2-continued

Biological activity

| Ex. | % inhibition at 10 μM |
|---|---|
| 8e | 97 |
| 8f | 99 |
| 8g | 98 |
| 8h | 100 |
| 9e | 20 |
| 9f | 54 |
| 9g | 79 |
| 10c | 100 |
| 11d | 100 |
| 11e | 98 |
| 11f | 98 |
| 12c | 85 |
| 13a | 48 |
| 13b | 100 |
| 13c | 100 |
| 14e | 97 |
| 14f | 100 |
| 15c | 0.3 |
| 16c | 0.01 |
| 17 | 0.01 |
| 18 | 0.02 |
| 19 | 1.0 |
| 20 | 0.04 |
| 21 | 0.3 |
| 22 | 1.1 |
| 23 | 0.03 |
| 24 | 0.09 |
| 25 | 0.06 |
| 26 | 0.04 |
| 27 | 0.02 |
| 28 | 0.04 |
| 29 | 0.01 |
| 30 | 0.02 |
| 31 | 0.01 |
| 32 | 0.03 |
| 33 | 1.0 |
| 34 | 3.2 |
| 35 | 0.3 |
| 36 | 0.3 |
| 37 | 3.9 |
| 38 | 4.6 |
| 39 | 0.01 |
| 40 | 4.6 |
| 41 | 0.01 |
| 42 | 0.01 |
| 43 | 0.15 |
| 44 | 0.05 |
| 45 | 0.8 |
| 46 | 0.01 |
| 47 | 0.01 |
| 48 | 0.01 |
| 49 | 0.01 |
| 50 | 0.01 |

It can be seen from the table that the compounds of the formula I inhibit the activity of glycogen phosphorylase a and thus reduce the blood sugar level.

We claim:

1. A compound of the formula I,

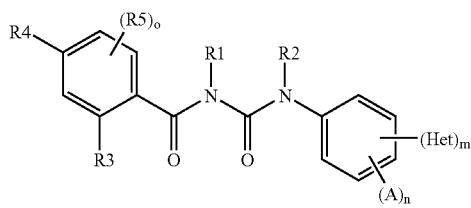

wherein

R1 and R2 are each independently H, O—$(C_1$–$C_6)$-alkyl, CO—$(C_1$–$C_6)$-alkyl, COO—$(C_1$–$C_6)$-alkyl, $(C_1$–$C_6)$-alkylene-COOH, $(C_1$–$C_6)$-alkylene-COO—$(C_1$–$C_6)$-alkyl or $(C_1$–$C_6)$-alkyl, wherein said $(C_1$–$C_6)$-alkyl is optionally substituted by OH, O—$(C_1$–$C_4)$-alkyl, $NH_2$, $NH(C_1$–$C_4)$-alkyl or $N[(C_1$–$C_6)$-alkyl]$_2$;

R3 and R4 are each independently F, Cl, Br, OH, $NO_2$, CN, $(C_1$–$C_6)$-alkyl, O—$(C_1$–$C_4)$-alkyl, O—$(C_2$–$C_6)$-alkenyl or $(C_2$–$C_6)$-alkynyl, wherein said $(C_1$–$C_6)$-alkyl, O—$(C_1$–$C_4)$-alkyl, O—$(C_2$–$C_6)$-alkenyl and $(C_2$–$C_6)$-alkynyl are optionally mono- or polysubstituted by F, Cl or Br;

R5 is H, F, Cl, Br, OH, $NO_2$, CN, $(C_1$–$C_6)$-alkyl, O—$(C_1$–$C_4)$-alkyl, CO—$(C_1$–$C_6)$-alkyl, $(C_0$–$C_6)$-alkylene-COOH, $(C_0$–$C_6)$-alkylene-COO—$(C_1$–$C_6)$-alkyl, $SO_2$—$(C_1$–$C_6)$-alkyl, O—$(C_2$–$C_6)$-alkenyl or $(C_2$–$C_6)$-alkynyl, wherein said $(C_1$–$C_6)$-alkyl, O—$(C_1$–$C_4)$-alkyl, CO—$(C_1$–$C_6)$-alkyl, $(C_0$–$C_6)$-alkylene-COOH, $(C_0$–$C_6)$-alkylene-COO—$(C_1$–$C_6)$-alkyl, $SO_2$—$(C_1$–$C_6)$-alkyl, O—$(C_2$–$C_6)$-alkenyl and $(C_2$–$C_6)$-alkynyl are optionally mono- or polysubstituted by F, Cl or Br;

A is H, F, Cl, Br, OH, $NO_2$, CN, $(C_1$–$C_6)$-alkyl, CO—$(C_1$–$C_6)$-alkyl, $(C_1$–$C_6)$-alkylene-COOH, $(C_1$–$C_6)$-alkylene-COO$(C_1$–$C_6)$-alkyl, $SO_2$—$(C_1$–$C_6)$-alkyl, $(C_2$–$C_6)$-alkenyl, $(C_2$–$C_6)$-alkynyl, O—$(C_1$–$C_6)$-alkyl, $S(O)_{1-2}$—$(C_1$–$C_6)$-alkyl-, NH—$(C_1$–$C_6)$-alkyl, N—$[(C_1$–$C_6)$-alkyl]$_2$, COO—$(C_1$–$C_6)$-alkyl, $CONH_2$, CONH—$(C_1$–$C_6)$-alkyl, CON—$[(C_1$–$C_6)$-alkyl]$_2$, $SO_2NH_2$, $SO_2NH$—$(C_1$–$C_6)$-alkyl, $SO_2N$—$[(C_1$–$C_6)$-alkyl]$_2$ or NHCOR6, wherein said $(C_1$–$C_6)$-alkyl, CO—$(C_1$–$C_6)$-alkyl, $(C_1$–$C_6)$-alkylene-COOH, $(C_1$–$C_6)$-alkylene-COO$(C_1$–$C_6)$-alkyl, $SO_2$—$(C_1$–$C_6)$-alkyl, $(C_2$–$C_6)$-alkenyl, $(C_2$–$C_6)$-alkynyl, O—$(C_1$–$C_6)$-alkyl, $S(O)_{1-2}$—$(C_1$–$C_6)$-alkyl-, NH—$(C_1$–$C_6)$-alkyl, N—$[(C_1$–$C_6)$-alkyl]$_2$, COO—$(C_1$–$C_6)$-alkyl, CONH—$(C_1$–$C_6)$-alkyl, CON—$[(C_1$–$C_6)$-alkyl]$_2$, $SO_2NH$—$(C_1$–$C_6)$-alkyl and $SO_2N$—$[(C_1$–$C_6)$-alkyl]$_2$ are optionally mono- or polysubstituted by F, Cl, Br, COOH, COO—$(C_1$–$C_6)$-alkyl, $CONH_2$, CONH—$(C_1$–$C_6)$-alkyl, CON$[(C_1$–$C_6)$-alkyl]$_2$ or OCO—$(C_1$–$C_6)$-alkyl;

R6 is H, $(C_1$–$C_6)$-alkyl, $(C_3$–$C_7)$-cycloalkyl, $(C_3$–$C_7)$-cycloalkyl-$(C_1$–$C_4)$-alkylene, $(C_2$–$C_6)$-alkenyl, $(C_2$–$C_6)$-alkynyl, $(C_1$–$C_6)$-alkylene-COO—$(C_1$–$C_6)$-alkyl, $(C_1$–$C_6)$-alkylene-CO—$(C_1$–$C_6)$-alkyl, $(C_0$–$C_6)$-alkylene-COOH, $(C_1$–$C_6)$-alkylene-$CONH_2$, $(C_6$–$C_{10})$-aryl, $(C_1$–$C_4)$-alkylene-$(C_6$–$C_{10})$-aryl, heteroaryl, $(C_1$–$C_4)$-alkylene-heteroaryl or CO-heteroaryl, wherein said $(C_1$–$C_6)$-alkyl, $(C_3$–$C_7)$-cycloalkyl, $(C_3$–$C_7)$-cycloalkyl-$(C_1$–$C_4)$-alkylene, $(C_2$–$C_6)$-alkenyl, $(C_2$–$C_6)$-alkynyl, $(C_1$–$C_6)$-alkylene-COO—$(C_1$–$C_6)$-alkyl, $(C_1$–$C_6)$-alkylene-CO—$(C_1$–$C_6)$-alkyl, $(C_0$–$C_6)$-alkylene-COOH and $(C_1$–$C_6)$-alkylene-$CONH_2$ are optionally mono- or polysubstituted by F, Cl, Br, $O(C_1$–$C_4$-alkyl), COO—$(C_1$–$C_4$-alkyl) or N—$[(C_1$–$C_4)$-alkyl]$_2$ and said $(C_6$–$C_{10})$-aryl, $(C_1$–$C_4)$-alkylene-$(C_6$–$C_{10})$-aryl, heteroaryl, $(C_1$–$C_4)$-alkylene-heteroaryl and CO-heteroaryl are optionally mono- or polysubstituted by F, Cl, Br, $NO_2$, CN, O—$(C_1$–$C_4$-alkyl), S—$COO(C_1$–$C_4$-alkyl), COO—$(C_1$–$C_4$-alkyl), N—$[(C_1$–$C_4)$-alkyl]$_2$ or $(C_1$–$C_6)$-alkyl;

n is 0, 1, 2 or 3;

m is 1, 2, 3, 4 or 5;

o is 0, 1, 2 or 3;

Het is a heterocyclic 4- to 7-membered ring which may contain up to four N, O or S heteroatoms and wherein said heterocyclic 4- to 7-membered ring is optionally substituted by R7, R8 and R9, with the proviso that said heterocyclic 4- to 7-membered ring cannot be pyrrole; and R7, R8, and R9 are each independently H, F, Cl, Br, $(C_1–C_6)$-alkyl, O—$(C_1–C_6)$-alkyl, O—$(C_2–C_6)$-alkenyl, O—$(C_2–C_6)$-alkynyl, OH, oxo, O—$(C_1–C_6)$-alkyl, $NH_2$, NH—$(C_1–C_6)$-alkyl, N—$[(C_1–C_6)$-alkyl$]_2$, COOH, CO—$(C_1–C_6)$-alkyl, COO—$(C_1–C_6)$-alkyl, $CONH_2$, CONH—$(C_1–C_6)$-alkyl, CON—$[(C_1–C_6)$-alkyl$]_2$, $(C_0–C_6)$-alkylene-aryl or $(C_1–C_6)$-alkylene-COO—$(C_1–C_6)$-alkyl, wherein said $(C_1–C_6)$-alkyl, O—$(C_1–C_6)$-alkyl, O—$(C_2–C_6)$-alkenyl, O—$(C_2–C_6)$-alkynyl, O—$(C_1–C_6)$-alkyl, NH—$(C_1–C_6)$-alkyl, N—$[(C_1–C_6)$-alkyl$]_2$, CO—$(C_1–C_6)$-alkyl, COO—$(C_1–C_6)$-alkyl, CONH—$(C_1–C_6)$-alkyl, CON—$[(C_1–C_6)$-alkyl$]_2$, $(C_0–C_6)$-alkylene-aryl and $(C_1–C_6)$-alkylene-COO—$(C_1–C_6)$-alkyl are optionally substituted by COOH, $CONH_2$, CONH—$(C_1–C_6)$-alkyl, CON—$[(C_1–C_6)$-alkyl$]_2$, OCO—$(C_1–C_6)$-alkyl, F, Cl, $(C_1–C_6)$-alkyl or O—$(C_1–C_6)$-alkyl;

and two radicals selected from said R7, R8 and R9 may optionally be bonded together to form a ring fused onto said heterocyclic 4- to 7-membered ring;

and pharmaceutically acceptable salts thereof.

2. The compound of claim 1 wherein

R1 and R2 are H;

R3 and R4 are each independently F, Cl or Br;

R5 is H, F, Cl, Br, OH, $NO_2$, CN, $(C_1–C_6)$-alkyl, O—$(C_1–C_4)$-alkyl, CO—$(C_1–C_6)$-alkyl, $(C_0–C_6)$-alkylene-COOH, $(C_0–C_6)$-alkylene-COO—$(C_1–C_6)$-alkyl, $SO_2$—$(C_1–C_6)$-alkyl, O—$(C_2–C_6)$-alkenyl or $(C_2–C_6)$-alkynyl, wherein said $(C_1–C_6)$-alkyl, O—$(C_1–C_4)$-alkyl, CO—$(C_1–C_6)$-alkyl, $(C_0–C_6)$-alkylene-COOH, $(C_0–C_6)$-alkylene-COO—$(C_1–C_6)$-alkyl, $SO_2$—$(C_1–C_6)$-alkyl, O—$(C_2–C_6)$-alkenyl and $(C_2–C_6)$-alkynyl are optionally mono- or polysubstituted by F, Cl or Br;

A is H, F, Cl, Br, OH, $NO_2$, CN, $(C_1–C_6)$-alkyl, CO—$(C_1–C_6)$-alkyl, $(C_1–C_6)$-alkylene-COOH, $(C_1–C_6)$-alkylene-COO$(C_1–C_6)$-alkyl, $SO_2$—$(C_1–C_6)$-alkyl, $(C_2–C_6)$-alkenyl, $(C_2–C_6)$-alkynyl, O—$(C_1–C_6)$-alkyl, $S(O)_{1-2}$—$(C_1–C_6)$-alkyl-, NH—$(C_1–C_6)$-alkyl, N—$[(C_1–C_6)$-alkyl$]_2$, COO—$(C_1–C_6)$-alkyl, $CONH_2$, CONH—$(C_1–C_6)$-alkyl, CON—$[(C_1–C_6)$-alkyl$]_2$, $SO_2NH_2$, $SO_2NH$—$(C_1–C_6)$-alkyl, $SO_2N$—$[(C_1–C_6)$-alkyl$]_2$ or $NHCOR6$, wherein said $(C_1–C_6)$-alkyl, CO—$(C_1–C_6)$-alkyl, $(C_1–C_6)$-alkylene-COOH, $(C_1–C_6)$-alkylene-COO$(C_1–C_6)$-alkyl, $SO_2$—$(C_1–C_6)$-alkyl, $(C_2–C_6)$-alkenyl, $(C_2–C_6)$-alkynyl, O—$(C_1–C_6)$-alkyl, $S(O)_{1-2}$—$(C_1–C_6)$-alkyl-, NH—$(C_1–C_6)$-alkyl, N—$[(C_1–C_6)$-alkyl$]_2$, COO—$(C_1–C_6)$-alkyl, CONH—$(C_1–C_6)$-alkyl, CON—$[(C_1–C_6)$-alkyl$]_2$, $SO_2NH$—$(C_1–C_6)$-alkyl and $SO_2N$—$[(C_1–C_6)$-alkyl$]_2$ are optionally mono- or polysubstituted by F, Cl, Br, COOH, COO—$(C_1–C_6)$-alkyl, $CONH_2$, CONH—$(C_1–C_6)$-alkyl, CON—$[(C_1–C_6)$-alkyl$]_2$ or OCO—$(C_1–C_6)$-alkyl;

R6 is H, $(C_1–C_6)$-alkyl, $(C_3–C_7)$-cycloalkyl, $(C_3–C_7)$-cycloalkyl-$(C_1–C_4)$-alkylene, $(C_2–C_6)$-alkenyl, $(C_2–C_6)$-alkynyl, $(C_1–C_6)$-alkylene-COO—$(C_1–C_6)$-alkyl, $(C_1–C_6)$-alkylene-CO—$(C_1–C_6)$-alkyl, $(C_0–C_6)$-alkylene-COOH, $(C_1–C_6)$-alkylene-$CONH_2$, $(C_6–C_{10})$-aryl, $(C_1–C_4)$-alkylene-$(C_6–C_{10})$-aryl, heteroaryl, $(C_1–C_4)$-alkylene-heteroaryl or CO-heteroaryl, wherein said $(C_1–C_6)$-alkyl, $(C_3–C_7)$-cycloalkyl, $(C_3–C_7)$-cycloalkyl-$(C_1–C_4)$-alkylene, $(C_2–C_6)$-alkenyl, $(C_2–C_6)$-alkynyl, $(C_1–C_6)$-alkylene-COO—$(C_1–C_6)$-alkyl, $(C_1–C_6)$-alkylene-CO—$(C_1–C_6)$-alkyl, $(C_0–C_6)$-alkylene-COOH and $(C_1–C_6)$-alkylene-$CONH_2$ are optionally mono- or polysubstituted by F, Cl, Br, O—$(C_1–C_4)$-alkyl, COO—$(C_1–C_4)$-alkyl), or N—$[(C_1–C_4)$-alkyl$]_2$, and said $(C_6–C_{10})$-aryl, $(C_1–C_4)$-alkylene-$(C_6–C_{10})$-aryl, heteroaryl, $(C_1–C_4)$-alkylene-heteroaryl and CO-heteroaryl are optionally mono- or polysubstituted by F, Cl, Br, $NO_2$, CN, O—$(C_1–C_4$-alkyl), COO—$(C_1–C_4$-alkyl), S—$COO(C_1–C_4$-alkyl), N—$[(C_1–C_4)$-alkyl$]_2$ or $(C_1–C_6)$-alkyl;

n is 0, 1 or 2;

m is 1;

o is 0 or 1;

Het is a heterocyclic 4- to 7-membered ring selected from triazolyl, tetrazolyl, oxadiazolyl, pyrazolyl, benzimidazolyl, furyl, triazinyl or

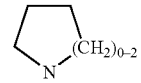

wherein said heterocyclic 4- to 7-membered ring is optionally substituted by R7, R8 and R9; and R7, R8, and R9 are each independently H, F, Cl, Br, $(C_1–C_6)$-alkyl, O—$(C_1–C_6)$-alkyl, O—$(C_2–C_6)$-alkenyl, O—$(C_2–C_6)$-alkynyl, OH, oxo, O—$(C_1–C_6)$-alkyl, $NH_2$, NH—$(C_1–C_6)$-alkyl, N—$[(C_1–C_6)$-alkyl$]_2$, COOH, CO—$(C_1–C_6)$-alkyl, COO—$(C_1–C_6)$-alkyl, $CONH_2$, CONH—$(C_1–C_6)$-alkyl, CON—$[(C_1–C_6)$-alkyl$]_2$, $(C_0–C_6)$-alkylene-aryl or $(C_1–C_6)$-alkylene-COO—$(C_1–C_6)$-alkyl, wherein said $(C_1–C_6)$-alkyl, O—$(C_1–C_6)$-alkyl, O—$(C_2–C_6)$-alkenyl, O—$(C_2–C_6)$-alkynyl, O—$(C_1–C_6)$-alkyl, NH—$(C_1–C_6)$-alkyl, N—$[(C_1–C_6)$-alkyl$]_2$, CO—$(C_1–C_6)$-alkyl, COO—$(C_1–C_6)$-alkyl, CONH—$(C_1–C_6)$-alkyl, CON—$[(C_1–C_6)$-alkyl$]_2$, $(C_0–C_6)$-alkylene-aryl and $(C_1–C_6)$-alkylene-COO—$(C_1–C_6)$-alkyl are optionally substituted by COOH, $CONH_2$, CONH—$(C_1–C_6)$-alkyl, CON—$[(C_1–C_6)$-alkyl$]_2$, OCO—$(C_1–C_6)$-alkyl, F, Cl, $(C_1–C_6)$-alkyl or O—$(C_1–C_6)$-alkyl;

and two radicals selected from said R7, R8 and R9 may optionally be bonded together to form a ring fused onto said heterocyclic 4- to 7-membered ring;

and pharmaceutically acceptable salts thereof.

3. The compound of claim 2 wherein

R1 and R2 are H;

R3 and R4 are each independently F, Cl or Br;

R5 is H, F, Cl, Br, OH, $NO_2$, CN, $(C_1–C_6)$-alkyl, O—$(C_1–C_4)$-alkyl, CO—$(C_1–C_6)$-alkyl, $(C_0–C_6)$-alkylene-COOH, $(C_0–C_6)$-alkylene-COO—$(C_1–C_6)$-alkyl, $SO_2$—$(C_1–C_6)$-alkyl, O—$(C_2–C_6)$-alkenyl or $(C_2–C_6)$-alkynyl, wherein said $(C_1–C_6)$-alkyl, O—$(C_1–C_4)$-alkyl, CO—$(C_1–C_6)$-alkyl, $(C_0–C_6)$-alkylene-COOH, $(C_0–C_6)$-alkylene-COO—$(C_1–C_6)$-alkyl, $SO_2$—$(C_1–C_6)$-alkyl, O—$(C_2–C_6)$-alkenyl and $(C_2–C_6)$-alkynyl are optionally mono- or polysubstituted by F, Cl or Br;

A is H, F, Cl, Br, $(C_1–C_6)$-alkyl, $CF_3$, $OCF_3$, $NO_2$, CN, O—$(C_1–C_6)$-alkyl, CO—$(C_1–C_6)$-alkyl, $(C_0–C_6)$-alkylene-COOH, $(C_0–C_6)$-alkylene-COO—$(C_1–C_6)$-alkyl, COO—$(C_1–C_6)$-alkyl or $SO_2$—$(C_1–C_6)$-alkyl;

n is 0, 1 or 2;

m is 1;

o is 0 or 1;

Het is a heterocyclic 4- to 7-membered ring group selected from triazolyl, tetrazolyl, oxadiazolyl, furyl, triazinyl or

[pyrrolidinyl structure with (CH₂)₀₋₂]

wherein said 4- to 7-membered heterocyclic ring is optionally substituted by R7, R8 and R9; and R7, R8, and R9 are each independently H, $(C_1-C_6)$-alkyl, OH, oxo, $NH_2$, COOH, COO—$(C_1-C_6)$-alkyl, $CONH_2$, CONH—$(C_1-C_6)$-alkyl or CON—$[(C_1-C_6)$-alkyl$]_2$, wherein said $(C_1-C_6)$-alkyl, COO—$(C_1-C_6)$-alkyl, CONH—$(C_1-C_6)$-alkyl and CON—$[(C_1-C_6)$-alkyl$]_2$ are optionally substituted by COOH;

and pharmaceutically acceptable salts thereof.

4. The compound of claim 1 wherein the compound has the structure Ia

[Structure Ia]

wherein

R5 is H, F, Cl, Br, $(C_1-C_6)$-alkyl, $CF_3$, $OCF_3$, $NO_2$, CN, O—$(C_1-C_6)$-alkyl, CO—$(C_1-C_6)$-alkyl, $(C_0-C_6)$-alkylene-COOH, $(C_0-C_6)$-alkylene-COO—$(C_1-C_6)$-alkyl or $SO_2$—$(C_1-C_6)$-alkyl;

A is H, F, Cl, Br, $(C_1-C_6)$-alkyl, $CF_3$, $OCF_3$, $NO_2$, CN, O—$(C_1-C_6)$-alkyl, CO—$(C_1-C_6)$-alkyl, $(C_0-C_6)$-alkylene-COOH, $(C_0-C_6)$-alkylene-COO—$(C_1-C_6)$-alkyl, COO—$(C_1-C_6)$-alkyl or $SO_2$—$(C_1-C_6)$-alkyl;

R7 is H, $(C_1-C_6)$-alkyl, $(C_0-C_6)$-alkylene-aryl, O—$(C_1-C_6)$-alkyl, O—$(C_2-C_6)$-alkenyl or O—$(C_2-C_6)$-alkynyl, wherein said $(C_1-C_6)$-alkyl, $(C_0-C_6)$-alkylene-aryl, O—$(C_1-C_6)$-alkyl, O—$(C_2-C_6)$-alkenyl and O—$(C_2-C_6)$-alkynyl are optionally mono- or polysubstituted by F, Cl or Br;

R8 is —(C=O)—X;

X is OH, O—$(C_1-C_6)$-alkyl, $NH_2$, NH—$(C_1-C_6)$-alkyl or N—$((C_1-C_6)$-alkyl$)_2$; and n is 1 or 2;

and pharmaceutically acceptable salts thereof.

5. The compound of claim 1 wherein the compound has the structure Iaa

[Structure Iaa]

wherein

R5 is H or F;

A is H, F, Cl, $(C_1-C_6)$-alkyl, $CF_3$, COO—$(C_1-C_6)$-alkyl, or $SO_2$—$(C_1-C_6)$-alkyl;

R7 is H or phenyl;

R8 is —(C=O)—X; and

X is OH, O—$(C_1-C_6)$-alkyl, $NH_2$, NH—$(C_1-C_6)$-alkyl or N—$[(C_1-C_6)$-alkyl$]_2$;

and pharmaceutically acceptable salts thereof.

6. A pharmaceutical composition comprising a pharmaceutically acceptable carrier and one or more compounds of claim 1.

7. A pharmaceutical composition comprising a pharmaceutically acceptable carrier and one or more compounds of claim 1 and at least one further active ingredient.

8. A method of reducing blood sugar comprising administering to a patient in need thereof a therapeutically effective amount of a compound of claim 1.

9. A method for treating lipid and carbohydrate metabolism disorders comprising administering to a patient in need thereof a therapeutically effective amount of a compound of claim 1.

10. A method for treating type 2 diabetes comprising administering to a patient in need thereof a therapeutically effective amount of a compound of claim 1.

11. A method for treating arteriosclerotic symptoms comprising administering to a patient in need thereof a therapeutically effective amount of a compound of claim 1.

12. A method for treating insulin resistance comprising administering to a patient in need thereof a therapeutically effective amount of a compound of claim 1.

13. A process for preparing a compound of claim 1, which comprises reacting a urea of formula 2 with a compound of formula 4

[Structure 2]

[Structure 4]

wherein

R1 and R2 are each independently H, O—$(C_1-C_6)$-alkyl, CO—$(C_1-C_6)$-alkyl, COO—$(C_1-C_6)$-alkyl, $(C_1-C_6)$-alkylene-COO H, $(C_1-C_6)$-alkylene-COO—$(C_1-C_6)$-alkyl or $(C_1-C_6)$-alkyl, wherein said $(C_1-C_6)$-alkyl is optionally substituted by OH, O—$(C_1-C_4)$-alkyl, $NH_2$, $N[(C_1-C_4)$-alkyl or $NH(C_1-C_6)$-alkyl$]_2$;

R3 and R4 are each independently F, Cl, Br, OH, $NO_2$, CN, $(C_1-C_6)$-alkyl, O—$(C_1-C_4)$-alkyl, O—$(C_2-C_6)$-alkenyl or $(C_2-C_6)$-alkynyl, wherein said $(C_1-C_6)$-alkyl, O—$(C_1-C_4)$-alkyl, O—$(C_2-C_6)$-alkenyl and $(C_2-C_6)$-alkynyl are optionally mono- or polysubstituted by F, Cl or Br;

R5 is H, F, Cl, Br, OH, $NO_2$, CN, $(C_1-C_6)$-alkyl, O—$(C_1-C_4)$-alkyl, CO—$(C_1-C_6)$-alkyl, $(C_0-C_6)$-alkylene-COOH, $(C_0-C_6)$-alkylene-COO—$(C_1-C_6)$-alkyl, $SO_2$—$(C_1-C_6)$-alkyl, O—$(C_2-C_6)$-alkenyl or $(C_2-C_6)$-alkynyl, wherein said $(C_1-C_6)$-alkyl, O—$(C_1-C_4)$- alkyl, CO—($C_1$–$C_6$)-alkyl, ($C_0$–$C_6$)-alkylene-COOH, ($C_0$–$C_6$)-alkylene-COO—($C_1$–$C_6$)-alkyl, $SO_2$—($C_1$–$C_6$)-alkyl, O—($C_2$–$C_6$)-alkenyl and ($C_2$–$C_6$)-alkynyl are optionally mono- or polysubstituted by F, Cl or Br;

A is H, F, Cl, Br, OH, $NO_2$, CN, ($C_1$–$C_6$)-alkyl, CO—($C_1$–$C_6$)-alkyl, ($C_1$–$C_6$)-alkylene-COOH, ($C_1$–$C_6$)-alkylene-COO($C_1$–$C_6$)-alkyl, $SO_2$—($C_1$–$C_6$)-alkyl, ($C_2$–$C_6$)-alkenyl, ($C_2$–$C_6$)-alkynyl, O—($C_1$–$C_6$)-alkyl, $S(O)_{1-2}$—($C_1$–$C_6$)-alkyl-, NH—($C_1$–$C_6$)-alkyl, N—[($C_1$–$C_6$)-alkyl]$_2$, COO—($C_1$–$C_6$)-alkyl, $CONH_2$, CONH—($C_1$–$C_6$)-alkyl, CON—[($C_1$–$C_6$)-alkyl]$_2$, $SO_2NH_2$, $SO_2NH$—($C_1$–$C_6$)-alkyl, $SO_2N$—[($C_1$–$C_6$)-alkyl]$_2$ or NHCOR6, wherein said ($C_1$–$C_6$)-alkyl, CO—($C_1$–$C_6$)-alkyl, ($C_1$–$C_6$)-alkylene-COOH, ($C_1$–$C_6$)-alkylene-COO($C_1$–$C_6$)-alkyl, $SO_2$—($C_1$–$C_6$)-alkyl, ($C_2$–$C_6$)-alkenyl, ($C_2$–$C_6$)-alkynyl, O—($C_1$–$C_6$)-alkyl, $S(O)_{1-2}$—($C_1$–$C_6$)-alkyl-, NH—($C_1$–$C_6$)-alkyl, N—[($C_1$–$C_6$)-alkyl]$_2$, COO—($C_1$–$C_6$)-alkyl, CONH—($C_1$–$C_6$)-alkyl, CON—[($C_1$–$C_6$)-alkyl]$_2$, $SO_2NH$—($C_1$–$C_6$)-alkyl and $SO_2N$—[($C_1$–$C_6$)-alkyl]$_2$ are optionally mono- or polysubstituted by F, Cl, Br, COOH, COO—($C_1$–$C_6$)-alkyl, $CONH_2$, CONH—($C_1$–$C_6$)-alkyl, CON[($C_1$–$C_6$)-alkyl]$_2$ or OCO—($C_1$–$C_6$)-alkyl;

n is 0, 1, 2 or 3;

R7 and R8 are each independently H, F, Cl, Br, ($C_1$–$C_6$)-alkyl, O—($C_1$–$C_6$)-alkyl, —O ($C_2$–$C_6$)-alkenyl, O—($C_2$–$C_6$)-alkynyl, OH, oxo, O—($C_1$–$C_6$)-alkyl, $NH_2$, NH—($C_1$–$C_6$)-alkyl, N—[($C_1$–$C_6$)-alkyl]$_2$, COOH, CO—($C_1$–$C_6$)-alkyl, COO—($C_1$–$C_6$)-alkyl, $CONH_2$, CONH—($C_1$–$C_6$)-alkyl, CON—[($C_1$–$C_6$)-alkyl]$_2$, ($C_0$–$C_6$)-alkylene-aryl or ($C_1$–$C_6$)-alkylene-COO—($C_1$–$C_6$)-alkyl, wherein said ($C_1$–$C_6$)-alkyl, O—($C_1$–$C_6$)-alkyl, O—($C_2$–$C_6$)-alkenyl, O—($C_2$–$C_6$)-alkynyl, O—($C_1$–$C_6$)-alkyl, NH—($C_1$–$C_6$)-alkyl, N—[($C_1$–$C_6$)-alkyl]$_2$, CO—($C_1$–$C_6$)-alkyl, COO—($C_1$–$C_6$)-alkyl, CONH—($C_1$–$C_6$)-alkyl, CON—[($C_1$–$C_6$)-alkyl]$_2$, ($C_0$–$C_6$)-alkylene-aryl and ($C_1$–$C_6$)-alkylene-COO—($C_1$–$C_6$)-alkyl are optionally substituted by COOH, $CONH_2$, CONH—($C_1$–$C_6$)-alkyl, CON—[($C_1$–$C_6$)-alkyl]$_2$, OCO—($C_1$–$C_6$)-alkyl, F, Cl, ($C_1$–$C_6$)-alkyl or O—($C_1$–$C_6$)-alkyl;

and said R7 and R8 may optionally be bonded together to form a ring fused onto said heterocyclic 4- to 7-membered ring; and Y is Cl or

[structure]

14. A process for preparing a compound of claim 1, which comprises reacting an aniline derivative of formula 3 with a compound of formula 4

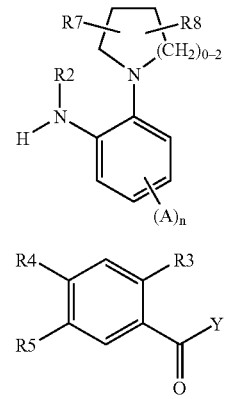

wherein

R2 is H, O—($C_1$–$C_6$)-alkyl, CO—($C_1$–$C_6$)-alkyl, COO—($C_1$–$C_6$)-alkyl, ($C_1$–$C_6$)-alkylene-COOH, ($C_1$–$C_6$)-alkylene-COO—($C_1$–$C_6$)-alkyl or ($C_1$–$C_6$)-alkyl, wherein said ($C_1$–$C_6$)-alkyl is optionally substituted by OH, O—($C_1$–$C_4$)-alkyl, $NH_2$, NH($C_1$–$C_4$)-alkyl or N[($C_1$–$C_6$)-alkyl]$_2$;

R3 and R4 are each independently F, Cl, Br, OH, $NO_2$, CN, ($C_1$–$C_6$)-alkyl, O—($C_1$–$C_4$)-alkyl, O—($C_2$–$C_6$)-alkenyl or ($C_2$–$C_6$)-alkynyl, wherein said ($C_1$–$C_6$)-alkyl, O—($C_1$–$C_4$)-alkyl, O—($C_2$–$C_6$)-alkenyl and ($C_2$–$C_6$)-alkynyl are optionally mono- or polysubstituted by F, Cl or Br;

R5 is H, F, Cl, Br, OH, $NO_2$, CN, ($C_1$–$C_6$)-alkyl, O—($C_1$–$C_4$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl, $SO_2$—($C_1$–$C_6$)-alkyl, O—($C_2$–$C_6$)-alkenyl or ($C_2$–$C_6$)-alkynyl, wherein said ($C_1$–$C_6$)-alkyl, O—($C_1$–$C_4$)-alkyl, CO—($C_1$–$C_6$)-alkyl, ($C_0$–$C_6$)-alkylene-COOH, ($C_0$–$C_6$)-alkylene-COO—($C_1$–$C_6$)-alkyl, $SO_2$—($C_1$–$C_6$)-alkyl, O—($C_2$–$C_6$)-alkenyl and ($C_2$–$C_6$)-alkynyl are optionally mono- or polysubstituted by F, Cl or Br;

A is H, F, Cl, Br, OH, $NO_2$, CN, ($C_1$–$C_6$)-alkyl, CO—($C_1$–$C_6$)-alkyl, ($C_1$–$C_6$)-alkylene-COOH, ($C_1$–$C_6$)-alkylene-COO($C_1$–$C_6$)-alkyl, $SO_2$—($C_1$–$C_6$)-alkyl, ($C_2$–$C_6$)-alkenyl, ($C_2$–$C_6$)-alkynyl, O—($C_1$–$C_6$)-alkyl, $S(O)_{1-2}$—($C_1$–$C_6$)-alkyl-, NH—($C_1$–$C_6$)-alkyl, N—[($C_1$–$C_6$)-alkyl]$_2$, COO—($C_1$–$C_6$)-alkyl, $CONH_2$, CONH—($C_1$–$C_6$)-alkyl, CON—[($C_1$–$C_6$)-alkyl]$_2$, $SO_2NH_2$, $SO_2NH$—($C_1$–$C_6$)-alkyl, $SO_2N$—[($C_1$–$C_6$)-alkyl]$_2$ or NHCOR6, wherein said ($C_1$–$C_6$)-alkyl, CO—($C_1$–$C_6$)-alkyl, ($C_1$–$C_6$)-alkylene-COOH, ($C_1$–$C_6$)-alkylene-COO($C_1$–$C_6$)-alkyl, $SO_2$—($C_1$–$C_6$)-alkyl, ($C_2$–$C_6$)-alkenyl, ($C_2$–$C_6$)-alkynyl, O—($C_1$–$C_6$)-alkyl, $S(O)_{1-2}$—($C_1$–$C_6$)-alkyl-, NH—($C_1$–$C_6$)-alkyl, N—[($C_1$–$C_6$)-alkyl]$_2$, COO—($C_1$–$C_6$)-alkyl, CONH—($C_1$–$C_6$)-alkyl, CON—[($C_1$–$C_6$)-alkyl]$_2$, $SO_2NH$—($C_1$–$C_6$)-alkyl and $SO_2N$—[($C_1$–$C_6$)-alkyl]$_2$ are optionally mono- or polysubstituted by F, Cl, Br, COOH, COO—($C_1$–$C_6$)-alkyl, $CONH_2$, CONH—($C_1$–$C_6$)-alkyl, CON[($C_1$–$C_6$)-alkyl]$_2$ or OCO—($C_1$–$C_6$)-alkyl;

n is 0, 1, 2 or 3;

R7 and R8 are each independently H, F, Cl, Br, ($C_1$–$C_6$)-alkyl, O—($C_1$–$C_6$)-alkyl, O—($C_2$–$C_6$)-alkenyl, O—($C_2$–$C_6$)-alkynyl, OH, oxo, O—($C_1$–$C_6$)-alkyl, $NH_2$, NH—($C_1$–$C_6$)-alkyl, N—[($C_1$–$C_6$)-alkyl]$_2$, COOH, CO—($C_1$–$C_6$)-alkyl, COO—($C_1$–$C_6$)-alkyl, $CONH_2$, CONH—($C_1$–$C_6$)-alkyl, CON—[($C_1$–$C_6$)-alkyl]$_2$, ($C_0$–$C_6$)-alkylene-aryl or ($C_1$–$C_6$)-alkylene-COO—($C_1$–$C_6$)-alkyl, wherein said ($C_1$–$C_6$)-alkyl, O—($C_1$–$C_6$)-alkyl, O—($C_2$–$C_6$)-alkenyl, O—($C_2$–$C_6$)-alkynyl, O—($C_1$–$C_6$)-alkyl, NH—($C_1$–$C_6$)-alkyl, N—[($C_1$–$C_6$)-alkyl]$_2$, CO—($C_1$–$C_6$)-alkyl, COO—($C_1$–$C_6$)-alkyl, CONH—($C_1$–$C_6$)-alkyl, CON—[($C_1$–$C_6$)-alkyl]$_2$, ($C_0$–$C_6$)-alkylene-aryl and ($C_1$–$C_6$)-alkylene-COO-($C_1$–$C_6$)-alkyl are optionally substituted by COOH, $CONH_2$, CONH—($C_1$–$C_6$)-alkyl, CON—[($C_1$–$C_6$)-alkyl]$_2$, OCO—($C_1$–$C_6$)-alkyl, F, Cl, ($C_1$–$C_6$)-alkyl or O—($C_1$–$C_6$)-alkyl;

and said R7 and R8 may optionally be bonded together to form a ring fused onto said heterocyclic 4- to 7-membered ring; and Y is —N═C═O.

15. A compoud which is 1-{2-[3-(2-chloro-4,5-difluorobenzoyl)ureido]-4- fluorophenyl}piperidine-4-carboxylic acid and pharmaceutically acceptable salts thereof.

* * * * *